US008795630B2

(12) United States Patent
Darvesh et al.

(10) Patent No.: US 8,795,630 B2
(45) Date of Patent: Aug. 5, 2014

(54) BUTYRYLCHOLINESTERASE LIGANDS AS DIAGNOSTIC TOOLS AND TREATMENT FOR DISEASES OF THE NERVOUS SYSTEM

(75) Inventors: Sultan Darvesh, Halifax (CA); Eric Joy, Lower Sackville (CA); Earl Martin, Halifax (CA); Ian Macdonald, Dartmouth (CA); Ian Pottie, Middle Sackville (CA)

(73) Assignee: Treventis Corporation, Bernville, PA (US)

( * ) Notice: Subject to any disclaimer, the term of this patent is extended or adjusted under 35 U.S.C. 154(b) by 341 days.

(21) Appl. No.: 13/061,000

(22) PCT Filed: Aug. 28, 2009

(86) PCT No.: PCT/US2009/055365
§ 371 (c)(1),
(2), (4) Date: May 23, 2011

(87) PCT Pub. No.: WO2010/025368
PCT Pub. Date: Mar. 4, 2010

(65) Prior Publication Data
US 2011/0212026 A1 Sep. 1, 2011

Related U.S. Application Data

(60) Provisional application No. 61/092,891, filed on Aug. 29, 2008.

(51) Int. Cl.
*A61K 51/04* (2006.01)
*A61K 31/54* (2006.01)
*B62B 3/02* (2006.01)

(52) U.S. Cl.
CPC .............. *B62B 3/022* (2013.01); *B62B 2205/12* (2013.01); *B62B 2202/404* (2013.01); *B62B 2205/24* (2013.01)
USPC ..... 424/1.85; 424/9.44; 424/9.45; 514/225.2; 514/252.13; 514/345; 514/351; 514/356

(58) Field of Classification Search
USPC ............ 424/1.85, 9.44, 9.45, 256; 514/225.2, 514/252.13, 345, 351, 356
See application file for complete search history.

(56) References Cited

U.S. PATENT DOCUMENTS

| | | | | |
|---|---|---|---|---|
| 4,038,396 | A | * | 7/1977 | Shen et al. ............... 514/302 |
| 6,544,986 | B2 | | 4/2003 | Darvesh et al. |
| 6,683,105 | B2 | | 1/2004 | Greig et al. |
| 7,442,475 | B2 | | 10/2008 | Farrand et al. |
| 2002/0094999 | A1 | | 7/2002 | Greig et al. |
| 2006/0165916 | A1 | | 7/2006 | Farrand et al. |
| 2008/0167343 | A1 | | 7/2008 | Ieni et al. |

FOREIGN PATENT DOCUMENTS

| | | |
|---|---|---|
| JP | 4095071 A | 3/1992 |
| JP | 06-263733 | 9/1994 |
| JP | 2001-500165 | 1/2001 |
| JP | 2006-077006 | 3/2006 |
| WO | WO 99/02154 | 1/1999 |
| WO | WO 01/77078 | 10/2001 |
| WO | WO 2004/074253 | 9/2004 |
| WO | WO 2006/065946 | 6/2006 |
| WO | WO 2007/035428 | 3/2007 |

OTHER PUBLICATIONS

Database Registry, Chemical Abstracts Service, Columbus, Ohio, Dec. 21, 2007, XP000002656838, Database accession No. 959352-48-8.
Database Registry, Chemical Abstracts Service, Columbus, Ohio, Aug. 28, 2001, XP000002656839, Database accession No. 353259-43-5.
Mikiciuk-Olaski, Elzbieta et al., "Diagnostics and therapy of Alzheimer's disease", Indian Journal of Experimental Biology (IJEB), Apr. 1, 2007, pp. 315-325.
Musial, Anna et al., "Recent Developments in Cholinesterases Inhibitors for Alzheimer's Disease Treatment", Current Medicinal Chemistry, Oct. 1, 2007, vol. 14, No. 25, pp. 2654-2679.

(Continued)

*Primary Examiner* — Michael G Hartley
*Assistant Examiner* — Jagadishwar Samala
(74) *Attorney, Agent, or Firm* — Davidson, Davidson & Kappel, LLC

(57) ABSTRACT

Compounds useful for the early diagnosis of malignant tumors, multiple sclerosis, and especially Alzheimer's Disease and related dementias; especially compounds of Formula (I) wherein $R_1$ is selected from the group consisting of hydrogen, cyano, fluoro, iodo, alkyl, and aryl; $R_2$ is selected from the group consisting of hydrogen, alkyl, and aryl; X is selected from the group consisting of $CH_2$, $CH_2O$, oxygen, $OCH_2$, $CH_2S$, $SCH_2$, NH, N-alkyl, and N-aryl; Y is an optional spacer group, absent or selected from the group consisting of oxygen, sulfur, NH, N-alkyl, and N-aryl; and Z is selected from the group consisting of alkyl substituted with cyano, fluoro, or iodo and aryl substituted with cyano, fluoro, or iodo. In a preferred embodiment, $R_1$ and $R_2$ are hydrogen, X is $CH_2O$, Y is absent, and Z is phenyl substituted with fluoro, cyano, or iodo. In some embodiments, Z is more specifically $^{18}$F-phenyl or $^{123}$I-phenyl or $^{131}$I-phenyl. Other compounds are also provided.

(I)

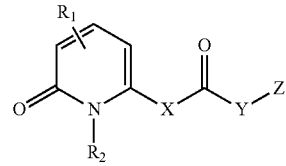

21 Claims, 4 Drawing Sheets

(56) References Cited

OTHER PUBLICATIONS

European Search Report issued in connection with corresponding International Application No. PCT/US2009/055365 dated Aug. 26, 2011.

International Search Report issued in connection with corresponding International Application No. PCT/US2009/055365.

Howard W. Chambers and John E. Casida, "Protective Activity of 1,3-Disubstituted 2- and 6-Pyridones against Selected Neurotoxic Agents," Toxicology and Applied Pharmacology, vol. 14, pp. 249-258, Apr. 29, 1968.

Bormans, G. et al "Synthesis of carbon-11- and fluorine-18-labeled 1-methyl-4-piperidyl-4'-fluorobenzoate and their biodistribution in mice" Nuclear Medicine and Biology, vol. 23, Issue 4, pp. 513-517, May 1996.

* cited by examiner

BUTYRYLCHOLINESTERASE LIGANDS AS DIAGNOSTIC TOOLS AND TREATMENT FOR DISEASES OF THE NERVOUS SYSTEM

CROSS-REFERENCE TO RELATED APPLICATIONS

This application is a National Stage of International Application No. PCT/US2009/055365 filed Aug. 28, 2009, which claims the benefit of U.S. Provisional Application Ser. No. 61/092,861 filed Aug. 29, 2008, which is hereby incorporated by reference in its entirety.

FIELD OF THE INVENTION

This invention relates to compounds for the early identification, treatment and diagnosis of Alzheimer's Disease and related diseases of the nervous system, especially as regards their use as contrast agents and/or radioligands in Computer Assisted Tomography, Single Photon Emission Computer Tomography, and/or Positron Emission Tomography. Such compounds also have utility as diagnostics for cancer and multiple sclerosis.

BACKGROUND OF THE INVENTION

Alzheimer's disease (AD) is a common neurodegenerative disorder causing dementia and a major cause of death. In AD there are three major microscopic features that are recognized as the hallmarks of the disease, namely, neuritic plaques (NP), neurofibrillary tangles (NFT) and amyloid angiopathy (AA). In addition, there is widespread cell loss, particularly of cholinergic neurons in the brain. Loss of cholinergic cells leads to reductions in the levels of the neurotransmitter acetylcholine (ACh), its synthesizing enzyme choline acetyltransferase, as well as its deactivating enzyme acetylcholinersterase (AChE). Reduction of cholinergic neurotransmission leads to some of the symptoms of AD. Because of this reduced cholinergic activity, drugs such as donepezil, metrifonate, rivastigmine, huperzine A, and tetrahydroaminoacridine, which inhibit the activity of cholinesterase and increase the level of ACh, have been used to treat the symptoms (though not the disease progression) of AD.

Determining when to begin therapy for AD is an extremely difficult task, however, because confirmation of the diagnosis of dementias such as AD is difficult at present and can only be truly confirmed by autopsy. Distinguishing between different forms of dementia such as AD, dementia with Lewy bodies, vascular dementia and frontotemporal dementia is challenging. Furthermore, early diagnosis of incipient dementia, such as mild cognitive impairment, becomes imperative for beginning symptomatic therapy, as well as when new disease-modifying AD drugs are developed. Thus, there remains a great need for a means of identifying and diagnosing AD at an early stage.

Neuroimaging is increasingly used to assist in diagnosis, but no satisfactory diagnostic tool has heretofore emerged. Structural imaging such as Computer Assisted Tomography (CAT) and Magnetic Resonance Imaging (MRI) provide information about changes in the brain, such as atrophy, stroke, malignancy and white matter changes, but at a gross anatomical level. Functional imaging using Single Photon Emission Computer Tomography (SPECT) and Positron Emission Tomography (PET) are non-specific. For example, one of the PET ligands used is $^{18}$-fluorodeoxyglucose and, for SPECT, $^{99m}$Tc hexa-methyl-propyl-amino oxime (HMPAO) or $^{99m}$Tc ethylene dicysteine di-ethyl ester (ECD). Each of these techniques provides information regarding reduced functional integrity of different parts of the brain, but do not provide information as to why there is reduced function in these regions. More recently, radioligands that bind to the AD-implicated β-amyloid protein have been developed (for example, AV-45). These ligands provide information as to whether, and where, β-amyloid is present in the brain. From a neuropathologic perspective, deposition of amyloid and formation of NP is one of the central mechanisms in the evolution of AD. However, amyloid plaques are also found in brains of elderly individuals who do not have dementia, which limits the applicability of this approach.

A technique of greater utility involves binding to cholinesterases, especially butyrylcholinesterase (BuChE). Although the level of AChE is reduced in AD, the level of the closely related enzyme BuChE is increased in AD brains. There is a severe loss of basal forebrain cholinergic neurons in AD (Coyle J. T., Price D. L., and DeLong M. R., 1983, Science 219:1184-90), and there is a marked decrease in the levels of AChE and a similarly marked increase in the levels of BuChE (Perry E. K., Perry R. H., Blessed G., and Tomlinson B. E., 1978, Neuropath. Appl. Neurobiol. 4:273-277; Mesulam M-M. and Geula C., 1994, Ann. Neurol. 36:722-727). BuChE is found in all the neuropathological lesions associated with AD (NP, NFT and AA). Amyloid plaques in individuals without dementia are "benign" and they become "malignant", causing dementia, when they are transformed into NP. Importantly, BuChE is found in NP in brains of patients with AD rather than plaques found in brains of elderly individuals without AD. Taken together, these observations show that in brains of patients with AD there is a significant alteration of the biochemical properties of BuChE that alters its normal regulatory role in the brain (Guillozet A. L., Smiley J. F., Mash D. C., and Mesulam M-M., 1997, Ann. Neurol. 42:909-918). As such, high affinity labeling of BuChE, particularly with radioligands, has utility in the early diagnosis of AD.

Within the context of detecting BuChE in the brain, only one experimental radioligand is available, namely, 1-[$^{11}$C]-methyl-4-piperidinyl n-butyrate. However, this compound has disadvantages. First, it is labeled with $^{11}$C, emitting positrons that can only be detected by PET scanners, which are not as widely available as SPECT scanners. Second, the radioactive label is attached to the molecule in the portion that is an initial leaving group in the mechanism of the enzyme catalyzed hydrolysis of this radiopharmaceutical. Thus, the radioactive atom intended to label the enzyme is lost in the early stages of the reaction, which would lead to short-lived enzyme-detecting capability of this ligand and only show diffuse distribution of the label rather than specific regional distribution of the target enzyme.

OBJECTS AND SUMMARY OF THE INVENTION

This application discloses molecules that overcome the shortcomings of previous radioligands and provide specific and long-lived radioligands for diagnosis and for monitoring treatment effects in AD. These compounds are specific substrates of BuChE and contain atoms that can be efficiently replaced with radioactive atoms in the moiety that is attached to BuChE for a longer period, to facilitate detection by SPECT or PET scanning. Such compounds are of utility in the early diagnosis and treatment of diseases associated with dysregulation of BuChE, including AD and related dementias, multiple sclerosis, and malignant tumors; and can distinguish AD brain from normal brain.

In certain embodiments, the invention is directed to BuChE ligands having a radiolabeled moiety that remains in contact with the enzyme after enzymatic cleavage, (e.g. hydrolysis), of the ligand. This arrangement allows the radiolabeled moiety to remain in contact with the enzyme for a greater duration.

The inventions is also directed to administration of therapeutically effective amounts of BuChE ligands which inhibit the enzyme for treatment of diseases associated with dysregulation of BuChE, including AD and related dementias, multiple sclerosis, and malignant tumors to a patient in need thereof.

It is an object of the invention to provide a compound of Formula I and pharmaceutically acceptable salts, stereo-isomers, polymorphs, metabolites, pro-drugs and combinations thereof:

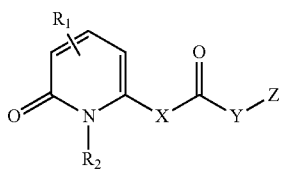

(I)

wherein $R_1$ is selected from the group consisting of hydrogen, cyano, fluoro, iodo, alkyl, and aryl; $R_2$ is selected from the group consisting of hydrogen, alkyl, and aryl; X is selected from the group consisting of $CH_2$, $CH_2O$, oxygen, $OCH_2$, $CH_2S$, $SCH_2$, NH, N-alkyl, and N-aryl; Y is an optional spacer group, absent or selected from the group consisting of oxygen, sulfur, NH, N-alkyl, and N-aryl; and Z is selected from the group consisting of alkyl substituted with cyano, fluoro, or iodo and aryl substituted with cyano, fluoro, or iodo. In certain embodiments, $R_1$ and $R_2$ are both hydrogen, X is $CH_2O$, Y is absent, and Z is selected from the group consisting of fluorophenyl, cyanophenyl, and iodophenyl. In certain embodiments, Z is selected from the group consisting of $^{18}F$-phenyl, $^{123}I$-phenyl, and $^{131}I$-phenyl. In certain other embodiments, the compound is (6-oxo-1,6-dihydropyridin-2-yl)methyl 4-$^{123}$iodobenzoate.

It is another object of the invention to provide a compound of Formula II and pharmaceutically acceptable salts, stereoisomers, polymorphs, metabolites, pro-drugs and combinations thereof:

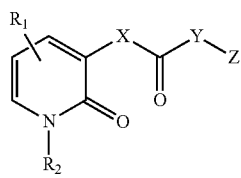

(II)

wherein $R_1$ is selected from the group consisting of hydrogen, cyano, fluoro, iodo, aryl, and alkyl; $R_2$ is selected from the group consisting of hydrogen, alkyl, and aryl; X is selected from the group consisting of $CH_2$, $CH_2O$, oxygen, $OCH_2$, $CH_2S$, $SCH_2$, NH, N-alkyl, and N-aryl; Y is an optional spacer group, absent or selected from the group consisting of oxygen, sulfur, NH, N-alkyl, and N-aryl; and Z is selected from the group consisting of alkyl substituted with cyano, fluoro, or iodo and aryl substituted with cyano, fluoro, or iodo. In certain embodiments, $R_1$ and $R_2$ are hydrogen, X is $CH_2O$, Y is absent, and Z is selected from the group consisting of cyanophenyl, fluorophenyl, and iodophenyl. In certain other embodiments, Z is selected from the group consisting of $^{18}F$-phenyl, $^{123}I$-phenyl, and $^{131}I$-phenyl.

It is another object of the invention to provide a compound of Formula III and pharmaceutically acceptable salts, stereoisomers, polymorphs, metabolites, pro-drugs and combinations thereof:

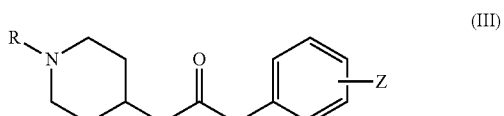

(III)

wherein R is selected from the group consisting of alkyl, alkyl-I, alkyl-F, alkyl-CN, aryl-I, aryl-CN, and aryl-F; X is an optional spacer group, absent or selected from the group consisting of oxygen, NH, N-alkyl, and N-aryl; Y is an optional spacer group, absent or selected from the group consisting of oxygen, sulfur, NH, N-alkyl, and N-aryl; and Z is selected from the group consisting of cyano, fluoro, and iodo. In certain embodiments, R is alkyl, X is oxygen, Y is absent or NH, and Z is selected from the group consisting of cyano, fluoro, and iodo. In certain other embodiments, Z is selected from the group consisting of $^{18}F$, $^{123}I$, and $^{131}I$.

It is another object of the invention to provide a compound of Formulas IVa and IVb and pharmaceutically acceptable salts, polymorphs, metabolites, pro-drugs and combinations thereof:

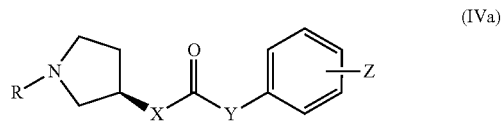

(IVa)

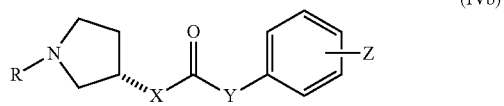

(IVb)

wherein R is selected from the group consisting of alkyl, alkyl-I, alkyl-F, alkyl-CN, aryl-I, aryl-CN, and aryl-F; X is an optional spacer group, absent or selected from the group consisting of oxygen, NH, N-alkyl, and N-aryl; Y is an optional spacer group, absent or selected from the group of oxygen, sulfur, NH, N-alkyl, and N-aryl; and Z is selected from the group of cyano, fluoro, and iodo. In certain embodiments, R is alkyl, X is oxygen, Y is absent, and Z is selected from the group consisting of iodo and cyano. In certain other embodiments, Z is selected from the group consisting of $^{18}F$, $^{123}I$, and $^{131}I$.

It is another object of the invention to provide a method of early detection of a neurological condition, comprising administering to a subject an effective quantity of a butyrylcholinesterase-specific compound; imaging the brain of said subject to identify the position and relative abundance of said compound in vivo utilizing a scan selected from the group consisting of CT, PET, and SPECT; and distinguishing said position and relative abundance from reference cases to determine subject's diagnosis. In certain embodiments, the butyrylcholinesterase-specific compound is the compound of formula I and pharmaceutically acceptable salts, stereo-isomers, polymorphs, metabolites, pro-drugs and combinations thereof. In certain other embodiments, the butyrylcholinesterase-specific compound is (6-oxo-1,6-dihydropyridin-2-yl)methyl 4-[123]iodobenzoate. In certain embodiments, the butyrylcholinesterase-specific compound is the compound of formula II and pharmaceutically acceptable salts, stereo-isomers, polymorphs, metabolites, pro-drugs and combinations thereof. In certain embodiments, the butyrylcholinesterase-specific compound is the compound of formula III and pharmaceutically acceptable salts, stereo-isomers, polymorphs, metabolites, pro-drugs and combinations thereof. In certain embodiments, the butyrylcholinesterase-specific compound is the compound of formula IV(a) and pharmaceutically acceptable salts, polymorphs, metabolites, pro-drugs and combinations thereof. In certain embodiments, the butyrylcholinesterase-specific compound is the compound of formula IV(b) and pharmaceutically acceptable salts, polymorphs, metabolites, pro-drugs and combinations thereof.

In accordance with any of the above objects, the invention is also directed to method in which the neurological condition is Alzheimer's disease and related dementias. In certain other embodiments, the neurological condition is multiple sclerosis. In certain other embodiments, the neurological condition is malignant brain tumor. In certain other embodiments, the subject is a human.

In accordance with any of the above objects, the invention is also directed to method in which the butyrylcholinesterase-specific compound is radiolabeled on a functional group of the compound that remains in contact with the BuChE after enzymatic cleavage of the compound It is another object of the invention to provide a method of treatment of a neurological condition, comprising:
administering to a subject in need thereof, an effective quantity of a butyrylcholinesterase-specific compound. In certain embodiments, the butyrylcholinesterase-specific compound is the compound of formula I and pharmaceutically acceptable salts, stereo-isomers, polymorphs, metabolites, pro-drugs and combinations thereof. In certain other embodiments, the butyrylcholinesterase-specific compound is (6-oxo-1,6-dihydropyridin-2-yl)methyl 4-iodobenzoate. In certain embodiments, the butyrylcholinesterase-specific compound is the compound of formula II and pharmaceutically acceptable salts, stereo-isomers, polymorphs, metabolites, pro-drugs and combinations thereof. In certain embodiments, the butyrylcholinesterase-specific compound is the compound of formula III and pharmaceutically acceptable salts, stereo-isomers, polymorphs, metabolites, pro-drugs and combinations thereof. In certain embodiments, the butyrylcholinesterase-specific compound is the compound of formula IV(a) and pharmaceutically acceptable salts, polymorphs, metabolites, pro-drugs and combinations thereof. In certain embodiments, the butyrylcholinesterase-specific compound is the compound of formula IV(b) and pharmaceutically acceptable salts, polymorphs, metabolites, pro-drugs and combinations thereof.

In accordance with any of the above objects, the invention is also directed to method in which the neurological condition is Alzheimer's disease and related dementias. In certain other embodiments, the neurological condition is multiple sclerosis. In certain other embodiments, the neurological condition is malignant brain tumor. In certain other embodiments, the subject is a human.

In accordance with any of the above objects, the invention is also directed to method in which the butyrylcholinesterase-specific compound is an inhibitor of butyrylcholinesterase.

DETAILED DESCRIPTION OF THE INVENTION

Figure 1:
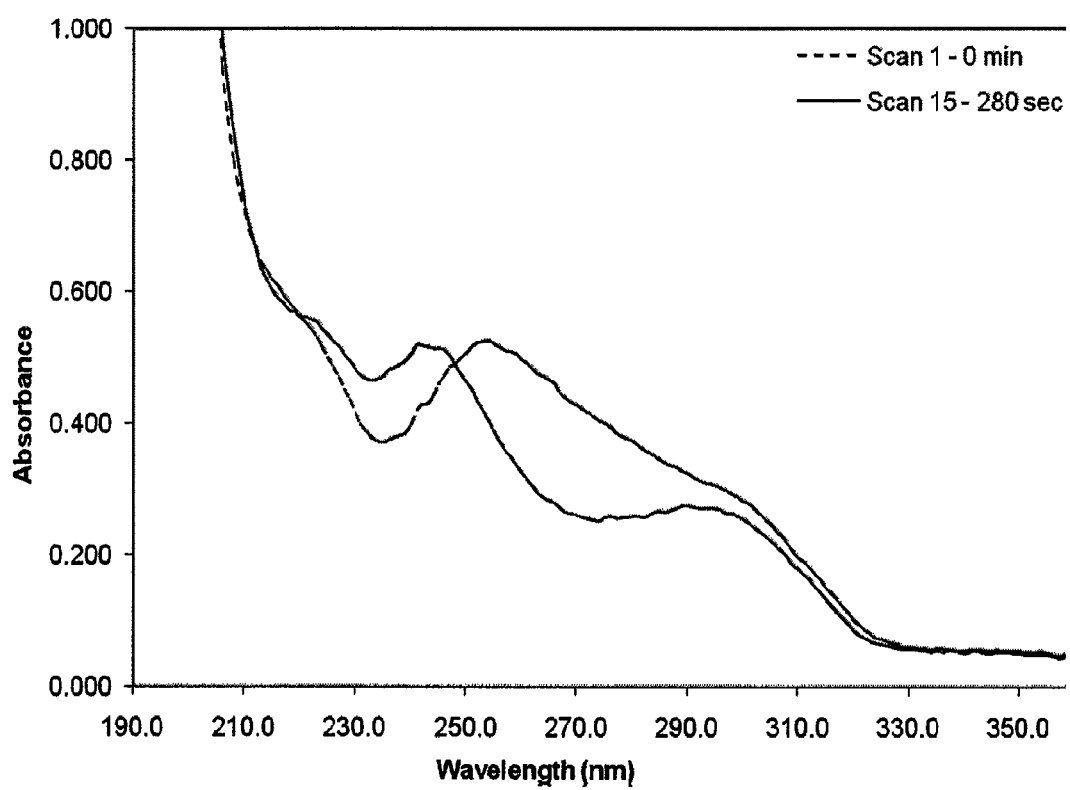
FIG. 1 is a repetitive scan of 1,6-dihydro-6-oxopyridin-2-yl)methyl 4-iodobenzoate in the presence of BuChE.
Figure 2:
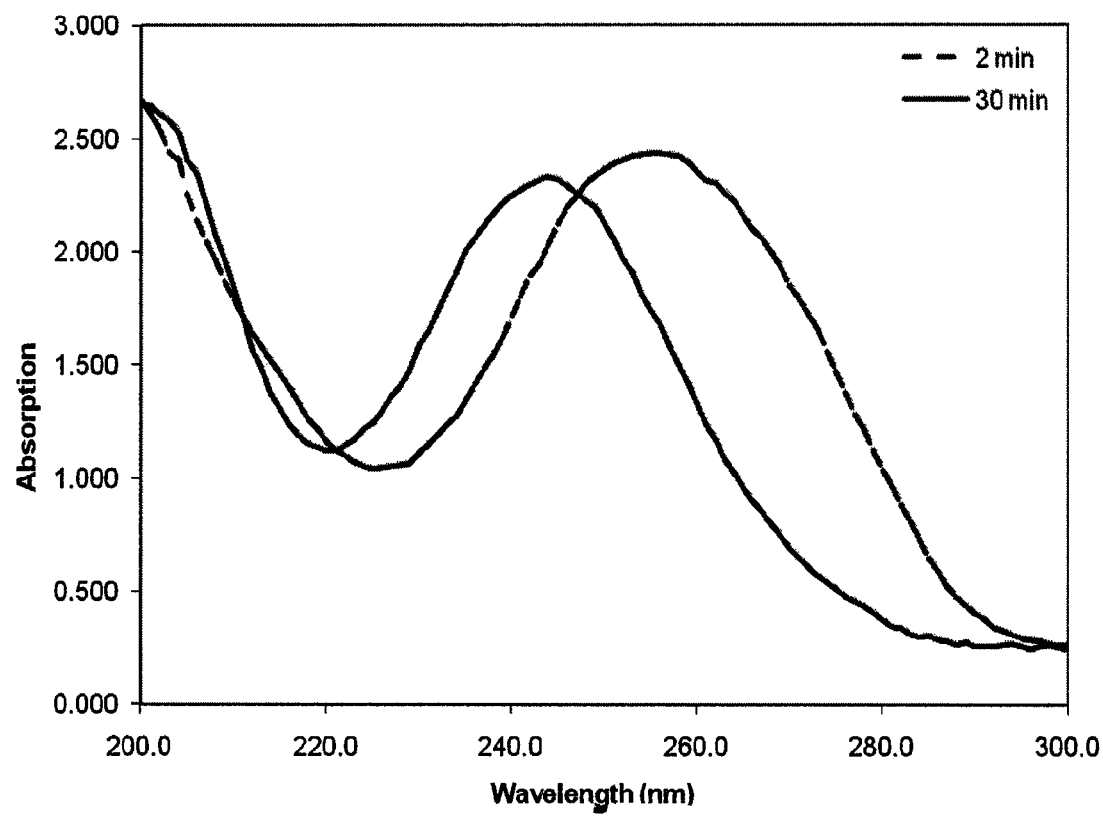
FIG. 2 is a repetitive scan of (S)-1-methylpyrrolidin-3-yl 4-iodobenzoate in the presence of BuChE.
Figure 3:
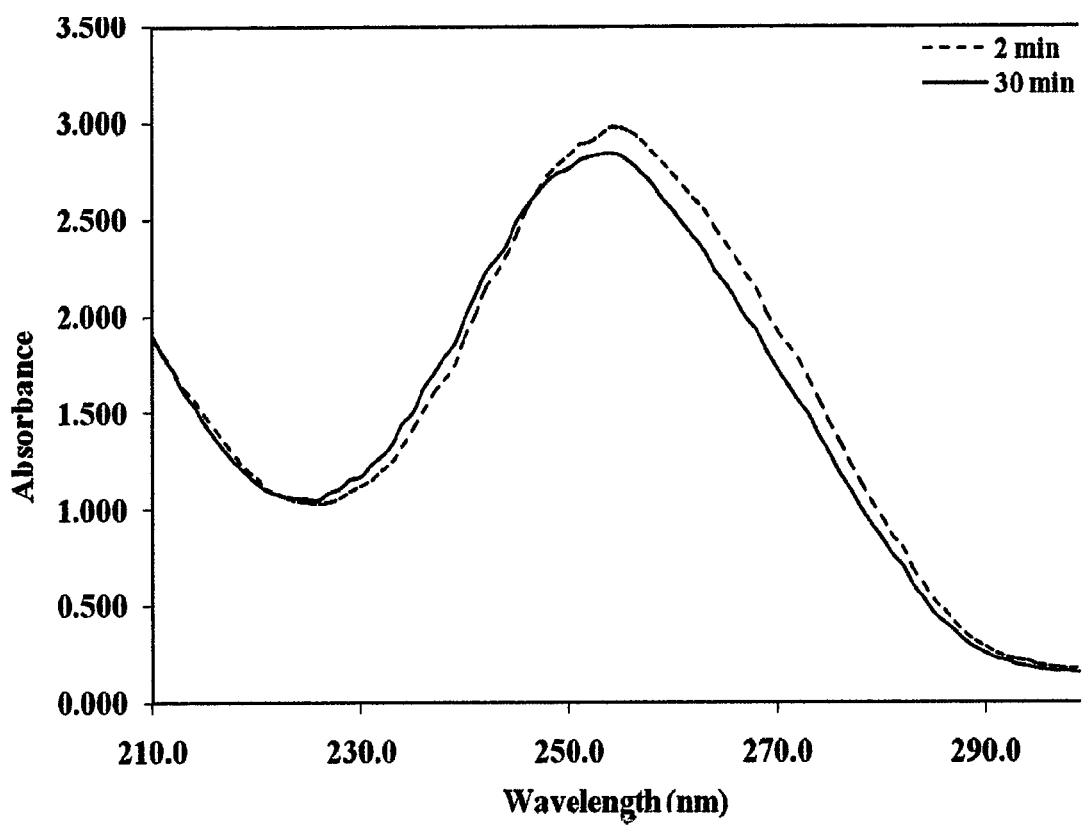
FIG. 3 is a repetitive scan of 1-methylpiperidin-4-yl 4-iodobenzoate in the presence of BuChE.

In accordance with the above-mentioned objects, one aspect of the present invention is directed to compounds of the following formulas.

The present invention is directed to compounds of Formula I and pharmaceutically acceptable salts, stereo-isomers, polymorphs, metabolites, pro-drugs and combinations thereof:

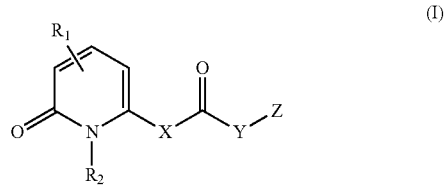

(I)

wherein $R_1$ is selected from the group consisting of hydrogen, cyano, fluoro, iodo, alkyl, and aryl; $R_2$ is selected from the group consisting of hydrogen, alkyl, and aryl; X is selected from the group consisting of $CH_2$, $CH_2O$, oxygen, $OCH_2$, $CH_2S$, $SCH_2$, NH, N-alkyl, and N-aryl; Y is an optional spacer group, absent or selected from the group consisting of oxygen, sulfur, NH, N-alkyl, and N-aryl; and Z is selected from the group consisting of alkyl substituted with cyano, fluoro, or iodo and aryl substituted with cyano, fluoro, or iodo. In a preferred embodiment, $R_1$ and $R_2$ are hydrogen, X is $CH_2O$, Y is absent, and Z is phenyl substituted with fluoro, cyano, or iodo. In a more preferred embodiment, Z is more specifically $^{18}F$-phenyl or $^{123}I$-phenyl or $^{131}I$-phenyl. It is to be understood that when Y is absent, Z directly connects to the carbonyl adjacent to Y with a bond order appropriate to the system, after considering, for example, aromaticity and tautomerism as applicable. In compounds where Y is absent and Z is phenyl substituted with fluoro, cyano, or iodo, it is to be understood that the phenyl ring directly connects to the carbonyl as described above and the phenyl substituent is connected in either ortho, meta, or para position with respect to the connection to carbonyl.

The invention is also directed to compounds of Formula II and pharmaceutically acceptable salts, stereo-isomers, polymorphs, metabolites, pro-drugs and combinations thereof:

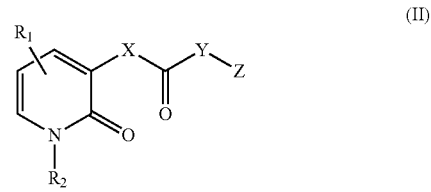

(II)

wherein $R_1$ is selected from the group consisting of hydrogen, cyano, fluoro, iodo, aryl, and alkyl; $R_2$ is selected from the group consisting of hydrogen, alkyl, and aryl; X is selected from the group consisting of $CH_2$, $CH_2O$, oxygen, $OCH_2$, CH₂S, SCH₂, NH, N-alkyl, and N-aryl; Y is an optional spacer group, absent or selected from the group consisting of oxygen, sulfur, NH, N-alkyl, and N-aryl; and Z is selected from the group consisting of alkyl substituted with cyano, fluoro, or iodo and aryl substituted with cyano, fluoro, or iodo. In preferred embodiments, R₁ and R₂ are hydrogen, X is CH₂O, Y is absent, and Z is phenyl substituted with cyano, fluoro, or iodo. In a more preferred embodiment, Z is more specifically ¹⁸F-phenyl or ¹²³I-phenyl or ¹³¹I-phenyl. It is to be understood that when Y is absent, Z directly connects to the carbonyl adjacent to Y with a bond order appropriate to the system, after considering, for example, aromaticity and tautomerism as applicable. In compounds where Y is absent and Z is phenyl substituted with fluoro, cyano, or iodo, it is to be understood that the phenyl ring directly connects to the carbonyl as described above and the phenyl substituent is connected in either ortho, meta, or para position with respect to the connection to carbonyl.

The invention is further directed to the compounds of Formula III and pharmaceutically acceptable salts, stereo-isomers, polymorphs, metabolites, pro-drugs and combinations thereof:

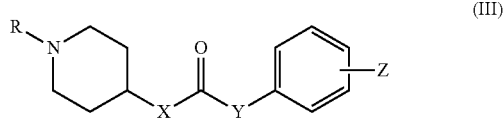

(III)

wherein R is selected from the group consisting of alkyl, alkyl-I, alkyl-F, alkyl-CN, aryl-I, aryl-CN, and aryl-F; X is an optional spacer group, absent or selected from the group consisting of oxygen, NH, N-alkyl, and N-aryl; Y is an optional spacer group, absent or selected from the group consisting of oxygen, sulfur, NH, N-alkyl, and N-aryl; and Z is selected from the group consisting of cyano, fluoro, and iodo. In preferred embodiments, R is alkyl, X is oxygen, Y is absent or NH, and Z is selected from the group consisting of cyano, fluoro, and iodo. In a more preferred embodiment, Z is more specifically ¹⁸F or ¹²³I or ¹³¹I. It is to be understood that when X is absent, the six-membered ring directly connects to the carbonyl adjacent to X in a manner such that the ring nitrogen is at the 4-position with respect to the connection point; and that the connection is a single carbon-carbon bond either cis or trans to the ring. It is to be understood that when Y is absent, the Z substituted phenyl directly connects to the carbonyl adjacent to Y with a single carbon-carbon bond; and Z is connected in either ortho, meta, or para position with respect to the connection to carbonyl.

The invention is also directed to enantiomeric compounds of Formulas IVa and IVb, as pharmaceutically acceptable salts, polymorphs, metabolites, pro-drugs and combinations thereof:

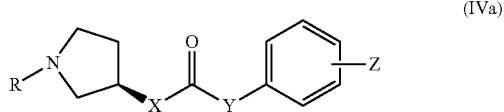

(IVa)

-continued

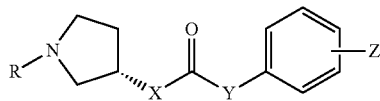

(IVb)

wherein R is selected from the group consisting of alkyl, alkyl-I, alkyl-F, alkyl-CN, aryl-I, aryl-CN, and aryl-F; X is an optional spacer group, absent or selected from the group consisting of oxygen, NH, N-alkyl, and N-aryl; Y is an optional spacer group, absent or selected from the group consisting of oxygen, sulfur, NH, N-alkyl, and N-aryl; and Z is selected from the group of cyano, fluoro, and iodo. In preferred embodiments, R is alkyl, X is oxygen, Y is absent or NH, and Z is iodo, fluoro or cyano. In a more preferred embodiment, Z is more specifically ¹⁸F or ¹²³I or ¹³¹I. It is to be understood that when X is absent, the five-membered ring directly connects to the carbonyl adjacent to X in a manner such that the ring nitrogen is at the 3-position with respect to the connection point; and that the connection is a single carbon-carbon bond either cis or trans to the ring. It is to be understood that when Y is absent, the Z substituted phenyl directly connects to the carbonyl adjacent to Y with a single carbon-carbon bond; and Z is connected in either ortho, meta, or para position with respect to the connection to carbonyl.

In certain embodiments, a method of early detection of Alzheimer's Disease and related dementias is provided, comprising administering to a subject an effective quantity of a butyrylcholinesterase-specific compound selected from the group consisting of compounds of formulae I, II, III, IVa and IVb and pharmaceutically acceptable salts, stereo-isomers, polymorphs, metabolites, pro-drugs and combinations thereof; imaging said subject to identify position and relative abundance of said compound in vivo utilizing CT, PET, and/or SPECT; and distinguishing said position and relative abundance from reference cases to determine subject's diagnosis. In a preferred embodiment, said subject is a human, and said imaging is of the subject's brain.

In certain embodiments, a method of early detection of multiple sclerosis is provided, comprising administering to a subject an effective quantity of a butyrylcholinesterase-specific compound selected from the group consisting of compounds of formulae I, II, III, IVa and IVb and pharmaceutically acceptable salts, stereo-isomers, polymorphs, metabolites, pro-drugs and combinations thereof; imaging said subject to identify position and relative abundance of said compound in vivo utilizing computed tomography ("CT"), PET, and/or SPECT; and distinguishing said position and relative abundance from reference cases to determine subject's diagnosis. In a preferred embodiment, said subject is a human, and said imaging is of the subject's brain.

In certain embodiments, a method of early detection of malignant tumors is provided, comprising administering to a subject an effective quantity of a butyrylcholinesterase-specific compound selected from the group consisting of compounds of formulae I, II, III, IVa and IVb and pharmaceutically acceptable salts, stereo-isomers, polymorphs, metabolites, pro-drugs and combinations thereof; imaging said subject to identify position and relative abundance of said compound in vivo utilizing CT, PET, and/or SPECT; and distinguishing said position and relative abundance from reference cases to determine subject's diagnosis. In a preferred embodiment, said subject is a human, and said imaging is of the subject's brain.

In certain embodiments, a method of treatment of diseases associated with dysregulation of BuChE, including AD and related dementias, multiple sclerosis, and malignant tumors, comprising administering to a subject in need thereof, an effective quantity of a butyrylcholinesterase-specific compound selected from the group consisting of compounds of formulae I, II, III, IVa and IVb and pharmaceutically acceptable salts, stereo-isomers, polymorphs, metabolites, prodrugs and combinations thereof.

It is of note that stable tri-alkyl tin derivatives of compounds described above (e.g. wherein cyano, iodo, or chloro groups within Z are replaced with a tri-alkyl tin moiety, preferably tri-butyl tin) are novel precursors of utility in the synthesis of radiolabeled compounds presented herein, and therefore present another embodiment. The process of making such derivatives is also an embodiment, as is the process of purifying the radiolabeled compounds presented herein.

In certain aspects of the invention, the compounds described herein can be considered as probes which, in conjunction with non-invasive neuroimaging techniques such as magnetic resonance spectroscopy ("MRS") or imaging ("MRI"), or gamma imaging such as positron emission tomography ("PET") or single-photon emission computed tomography ("SPECT"), can be used to identify neuritic plaques ("NP"). For in vivo imaging, detection instrument availability greatly affects selection of a given label. The type of instrument used will guide the selection of the radionuclide or stable isotope. For instance, the radionuclide chosen (e.g. $^{18}$F, $^{123}$I, or $^{131}$I) will have a type of decay detectable by a given type of instrument. Another consideration relates to the half-life of the radionuclide. Preferably, the half-life is long enough so that it is still detectable at the time of maximum uptake by the target, but short enough so that the host does not sustain deleterious radiation. Appropriately radiolabeled compounds as described herein can be detected using gamma imaging wherein emitted gamma irradiation of the appropriate wavelength is detected. Methods of gamma imaging include, but are not limited to, SPECT and PET.

The diagnostic or therapeutic compounds are administered to a subject by a route which is effective for diagnostic or therapeutic purposes. Suitable routes of administration include but are not limited to oral, subcutaneous, intravenous, sublingual, intraarterial, and intrathecal, intradermal, intracavitary, and intraperitoneal. A preferred route of administration is intravenous administration. The therapeutic compounds may be administered with a pharmaceutically acceptable vehicle. Particularly preferred pharmaceutical compositions are those that, in addition to selectively binding BuChE at high affinity and crossing the blood brain barrier, are also non-toxic at appropriate dosage levels and have a satisfactory duration of effect. Effective quantities will vary depending on such factors as subject weight, age, and potency of a given compound, and can be selected based on qualifying biodistribution and occupancy studies in a similarly sized subject.

The compounds of the present invention may be incorporated into various pharmaceutically acceptable dosage forms, including but not limited to oral and parenteral dosage forms. Oral dosage forms may include tablets, capsules, liquids, and the like. Parenteral dosage forms may include, but are not limited to dosage forms for intravenous, subcutaneous, intramuscular, intraperitoneal, intraarterial, and intradermal administration. The dosage forms of the present invention will contain a therapeutically effective amount of a compound(s) described herein such that the therapeutically effective dose is sufficient to inhibit BuChE activity in a subject.

In addition to containing a therapeutically effective amount of a compound(s) described herein, the dosage formulations may also contain pharmaceutically acceptable excipients. For example, the compositions of the present invention may contain a pharmaceutically acceptable diluent, including but not limited to monosaccharides, disaccharides, polyhydric alcohols and mixtures of two or more thereof. Preferred pharmaceutical diluents include, for example, starch, lactose, dextrose, mannitol, sucrose, microcrystalline cellulose, sorbitol, xylitol, fructose, and mixtures of two or more thereof.

In other embodiments, the pharmaceutical diluent is water-soluble, such as lactose, dextrose, mannitol, sucrose, or mixtures of two or more thereof.

Other suitable excipients for use in the compositions of the present invention include, but are not limited to, for example, poly(ethylene-vinyl acetate), copolymers of lactic acid and glycolic acid, poly(lactic acid), gelatin, collagen matrices, polysaccharides, poly(D,L lactide), poly(malic acid), poly (caprolactone), celluloses, albumin, starch, casein, dextran, polyesters, ethanol, methacrylate, polyurethane, polyethylene, vinyl polymers, glycols, mixtures thereof and the like.

Other excipients may include, but are not limited to, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthalate, noncrystalline cellulose, magnesium aluminum silicate, triethanolamine, polyvinyl alcohol, polyvinylpyrrolidone, sugars and starches. See, for example, Remington: The Science and Practice of Pharmacy, 1995, Gennaro ed.

As will be apparent to one knowledgeable in the art, specific excipients known in the art may be selected based on their properties and release characteristics in view of the intended use. Specifically, the carrier may be pH-sensitive, thermo-sensitive, thermo-gelling, arranged for sustained release or a quick burst. In some embodiments, carriers of different classes may be used in combination for multiple effects, for example, a quick burst followed by sustained release.

In other embodiments, one or more of the compounds in the invention may be encapsulated for delivery. Specifically, the compounds may be encapsulated in biodegradable microspheres, microcapsules, microparticles, or nanospheres. The delivery vehicles may be composed of, for example, hyaluronic acid, polyethylene glycol, poly(lactic acid), gelatin, poly(ε-caprolactone), or a poly(lactic-glycolic) acid polymer. Combinations may also be used, as, for example, gelatin nanospheres may be coated with a polymer of poly(lactic-glycolic) acid. As will be apparent to one knowledgeable in the art, these and other suitable delivery vehicles may be prepared according to protocols known in the art and utilized for delivery of the compounds.

It is of note that the compounds of the invention may be combined with permeation enhancers known in the art for improving delivery. Examples of permeation enhancers include, but are by no means limited to those compounds described in U.S. Pat. Nos. 3,472,931; 3,527,864; 3,896,238;

3,903,256; 3,952,099; 4,046,886; 4,130,643; 4,130,667; 4,299,826; 4,335,115; 4,343,798; 4,379,454; 4,405,616; 4,746,515; 4,788,062; 4,820,720; 4,863,738; 4,863,970; and 5,378,730; British Pat. No. 1,011,949; and Idson, 1975, J. Pharm. Sci. 64:901-924.

When the compounds of the invention are used for diagnosis, after a sufficient time has elapsed for the compound to bind BuChE (in a range between 30 minutes and 48 hours, for example), the area of the subject under investigation is examined by routine imaging techniques such as MRS/MRI, SPECT, PET, and CT. The exact protocol will necessarily vary depending upon factors specific to the patient, as noted above, and depending upon the body site under examination, method of administration and type of label used.

For the production of radioligands: compounds with a leaving group such as a tributyl tin, triflates or tosylates is dissolved in an appropriate solvent. To exchange the leaving group for iodine, the compound is treated with the appropriate reagent to incorporate radio-iodide. The exchange for fluorine is done using sodium fluoride. These reactions are carried out until the starting material has disappeared using thin layer chromatography, ("TLC") analysis. The acetone is then evaporated in vacuo and the product dissolved in dichloromethane, washed with water and the organic solution will be dried over magnesium sulfate and the solvent evaporated in vacuo. The product is purified either by crystallization or silica gel column chromatography and characterized using 500 mHz $^1$H NMR, $^{13}$C NMR, IR, and high resolution mass spec.

Radio-iodination labeling involves substitution of the precursor with an appropriate leaving group. The chemical reagent grade radionuclides are commercially available ($^{123}$I NaI, $^{131}$I NaI) as sodium iodide in sodium hydroxide solution. Precursors for radio-iodination include molecules with leaving groups such as tri-butyl tin, triflate and tosylate derivatives. The radiolabeled molecules are meant to be used for enzymatic assessment and binding assays. $^{131}$I Labeling is performed using iodobead or iodogen as a free radical initiator. The precursor is dissolved in an appropriate solvent and incubated with $^{131}$I sodium iodide.

Radio-fluorination labeling of $^{18}$F can be obtained as either the $F^-$ or $F_2$ form, depending on the irradiation conditions within a cyclotron. A common production method of $^{18}$F isotopes involves proton irradiation of [$^{18}$O] $H_2O$ to yield [$^{18}$F] as an F anion. A protective synthesis box is used, and reagents for the synthesis of [$^{18}$F] FDG can be adapted for a simple synthesis using [$^{18}$F] anion on a triflate derivative of the molecule to be labeled.

The following are presented as examples which should not be construed as further limiting the subject invention. The contents of all references and published patent applications cited throughout this application are hereby incorporated by reference.

Methods

Scheme one shows a method for preparing 6-substituted ester compounds. The readily available 6-hydroxypicolinic acid was reduced with lithium aluminum hydride to the corresponding 6-hydroxy methyl 2-hydroxypyridine. This can be treated with sodium hydride or butyl lithium to generate the alkoxide ion species which can be reacted with unsubstituted or substituted benzyl acid chlorides to afford a variety of esters of the general formula I.

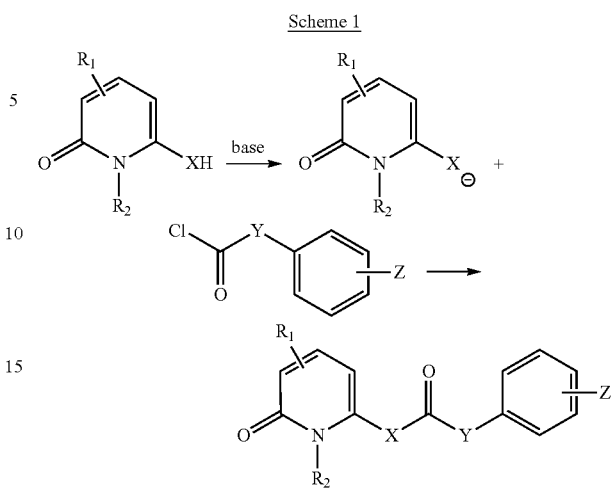

Scheme two presents a method for preparing 3-substituted ester compounds. The readily available 2-hydroxynicotinic acid was reduced with lithium aluminum hydride to the corresponding 3-hydroxy methyl 2-hydroxypyridine (1). This can be treated with either sodium hydride or butyl lithium to afford the alkoxide ion species which can be reacted with unsubstituted or substituted benzyl acid chlorides to produce a variety of esters of the general formula II.

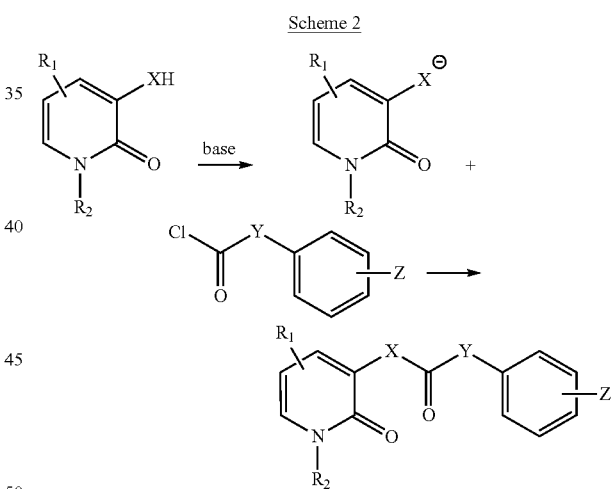

Scheme 3 presents a method for preparing 4-substituted ester compounds. The readily available 4-hydroxy-1-methylpiperidine was converted with butyl lithium to its corresponding alkoxide ion species which can be reacted with unsubstituted or substituted benzyl acid chlorides to produce a variety of esters of the general formula III.

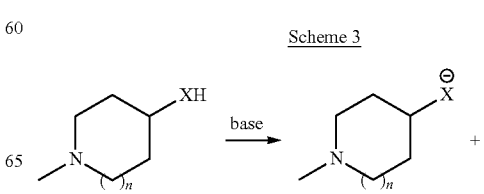

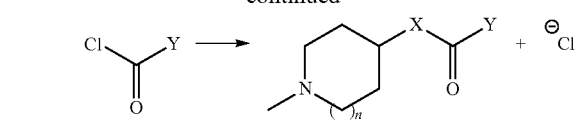

n = 0, 1
X = O, S
Y = alkyl or aryl with a halogen (I, Br, F) or nitrile

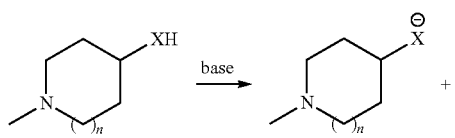

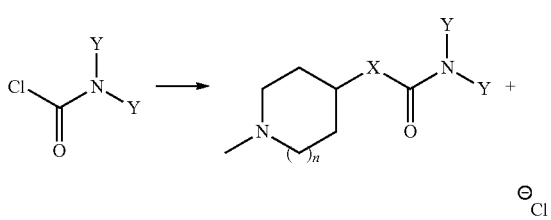

n = 0, 1
X = O, S
Y = alkyl or aryl with a halogen (I, Br, F) or nitrile

Scheme 4 presents a method for preparing 4-substituted ester compounds. The readily available (S)-(+)-1-methyl-3-pyrrolidinol was converted with butyl lithium to its corresponding alkoxide ion species which can be reacted with unsubstituted or substituted benzyl acid chlorides to produce a variety of esters of the general formula Iva/Ivb.

Scheme 4

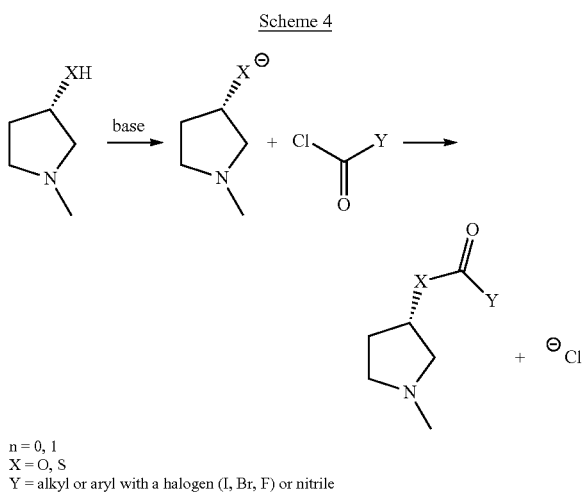

n = 0, 1
X = O, S
Y = alkyl or aryl with a halogen (I, Br, F) or nitrile

Scheme 5 presents a method for preparing 4-substituted ester compounds. The readily available R-(−)-1-methyl-3-pyrrolidinol was converted with butyl lithium to its corresponding alkoxide ion species which can be reacted with unsubstituted or substituted benzyl acid chlorides to produce a variety of esters of the general formula IV.

Scheme 5

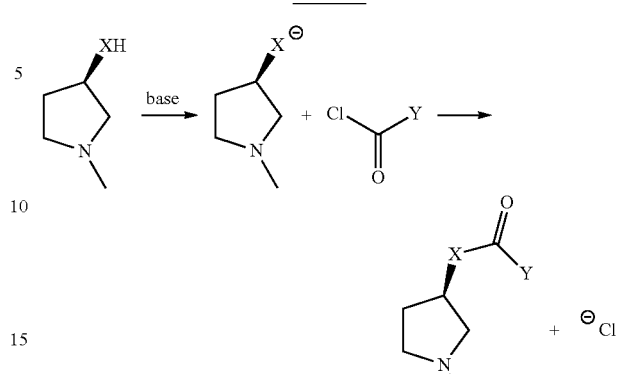

n = 0, 1
X = O, S
Y = alkyl or aryl with a halogen (I, Br, F) or nitrile

DETAILED DESCRIPTION OF PREFERRED EMBODIMENTS

Example 1

(1,2-dihydro-2-oxopyridin-3-yl)methyl 4-iodobenzoate

In Example 1, 1.6063 g (42.33 mmol) of lithium aluminum hydride (LAH) was suspended in 100 mL of tetrahydrofuran (THF) in a 250 mL round bottom flask (RBF) under the presence of argon gas (99.999% purity) and was cooled to 0° C. in an ice bath. 5.0946 g (36.62 mmol) of 2-hydroxynicotinic acid was slowly added, and the solution returned to room temperature before being refluxed for 8 h. The reaction was cooled to room temperature and was quenched with 1.6 mL of water, 1.6 mL of 15% NaOH and an additional 4.8 mL of water. The solvent was removed in vacuo and the residue was taken up in 100 mL of refluxing ethanol. The solution was filtered through celite and the solvent removed in vacuo to produce 1.4848 g (32.40% yield) of 3-hydroxymethyl-2-pyridone. Characterization data of the product was consistent with literature.

A 25 mL round bottom flask was charged with 0.209 g (1.67 mmole) of 3-(hydroxymethyl)pyridine-2(1H)-one and suspended in 15 mL of THF under the presence of argon gas. The solution was cooled to −80° C. in a methanol bath and 1.05 mL (1.68 mmol) of butyl lithium (BuLi) was added dropwise, and the solution stirred for 20 min. 0.4454 g (1.67 mmol) of 4-iodobenzoyl chloride was dissolved in 15 mL of THF, cooled to −80° C. in a methanol bath, then added dropwise into the alcohol reaction mixture. The reaction was stirred for 48 hours at −80° C. under the presence of argon gas. The reaction was then returned to room temperature and was quenched with 20 mL of water. The reaction was washed with ethyl acetate (4×20 mL), the organic layers combined, washed with Brine (3×20 mL), and finally dried over $MgSO_4$. The solvent was removed in vacuo to produce a dull brown solid. The compound was purified by crystallization from toluene. The yield of the product was 0.0652 g (10.99% Yield). MP: 203-205° C. IR: $(cm^{-1})$: 3415.21 (m, broad), υ (O—H), 3128.97 (m, broad), υ (N—H), 1720.30 (m), υ (C=O), 1613.77 (m), υ (C=C aromatic). $^1$H NMR (DMSO-$d_6$, 500 MHz) δ: 5.13 (s, 2H), 6.23 (t, J=6.6 Hz, 1H), 7.40 (dd, J=4.5, 2.1 Hz, 1H), 7.59 (dd, J=4.7, 2.1 Hz, 1H), 7.74 (d, J=4.8 Hz, 2H), 7.94 (d, J=4.8 Hz, 2H), 11.78 (s, 1H). $^{13}$C NMR (DMSO-d$_6$) δ: 165.76, 161.84, 139.75, 138.29, 135.79, 131.41, 129.58, 126.43, 105.09, 102.35, 62.81. HRMS: m/e, found 377.9583 (M$^+$Na$^+$). Calc. for C$_{13}$H$_{10}$INO$_3$Na: 377.9603.

Example 2

(1,2-dihydro-2-oxopyridin-3-yl)methyl 4-fluorobenzoate

In Example 2, 0.0725 g of 60% sodium hydride (NaH) was dispersed in mineral oil (1.60 mmol) and was suspended in 40 mL of THF in a 100 mL RBF under the presence of argon gas. Then, 0.2003 g (1.60 mmol) of 3-(hydroxymethyl)pyridine-2(1H)-one was added slowly and the solution stirred for 30 min with gentle heating before 0.250 mL (2.08 mmol) of 4-fluorobenzoyl chloride was added dropwise. The reaction was allowed to stir with gentle heating and for 48 hours. The reaction was quenched with the addition of 20 mL of water. The reaction was washed with ethyl acetate (4×20 mL) and the organic layers combined. The organic layer was washed with brine (3×20 mL) and dried over MgSO$_4$. The solvent was evaporated in vacuo to produce a white solid. The product was purified by crystallization from toluene. The yield of the reaction was 0.0590 g (14.94% yield). MP: 170-173° C. IR (cm$^{-1}$): 3415.21 (m, broad), υ (O—H), 3125.47 (m, broad), υ (N—H), 1716.90 (m), υ (C=O), 1614.44 (m), (C=C aromatic). $^1$H NMR (DMSO-d$_6$, 500 MHz) δ: 5.13 (s, 2H), 6.23 (t, J=6.6 Hz, 1H), 7.37 (t, J=8.9 Hz, 2H), 7.41 (dd, J=4.5, 2.1 Hz, 1H), 7.59 (dd, J=4.7, 2.1 Hz, 1H), 8.06 (t, J=7.7 Hz, 2H), 11.78 (s, 1H).

Example 3

(1,2-dihydro-2-oxopyridin-3-yl)methyl 4-cyanobenzoate

In Example 3, 0.0723 g of 60% NaH was dispersed in mineral oil (0.64 mmol) and was suspended in 50 mL of THF in a 100 mL RBF under the presence of argon gas. Then, 0.2026 g (1.62 mmol) of 3-(hydroxymethyl)pyridine-2(1H)-one was slowly added into the solution. This solution was stirred for 30 min with gentle heating before 0.2661 g (1.61 mmol) of 4-cyanobenzoyl chloride was added. The reaction was stirred with gentle heating for 48 hours. The reaction was quenched with 20 mL of and was washed with ethyl acetate (4×20 mL) and the organic layers combined. The organic layer was washed with brine (3×20 mL) before being dried of MgSO$_4$. The solvent was evaporated in vacuo to produce a white solid. The product was purified with silica gel column chromatography using 10% methanol in dichloromethane as eluent. The yield of the reaction was 0.1175 g (28.54% yield). MP: 200-203° C. IR (cm$^{-1}$): 3406.04 (m, broad), υ (O—H), 3113.07 (m, broad), υ (N—H), 1728.71 (m), υ (C=O), 1617.96 (s), υ (C=C aromatic). $^1$H NMR (DMSO-d$_6$, 500 MHz) δ: 5.17 (s, 2H), 6.23 (t, J=6.6 Hz, 1H), 7.42 (dd, J=4.5, 2.0 Hz, 1H), 7.63 (dd, J=4.7, 1.1 Hz, 1H), 8.02 (d, J=4.8 Hz, 2H), 8.10 (d, J=4.7, 2H), 11.80 (s, 1H).

Example 4

(1,6-dihydro-6-oxopyridin-2-yl)methyl 4-iodobenzoate

In Example 4, 4.0291 g (106.17 mmol) of lithium aluminum hydride was suspended in 150 mL of THF in a 250 mL RBF under the presence of argon gas and cooled to 0° C. in an ice bath. Then, 9.9990 g (71.88 mmol) of 6-hydroxypicolinic acid was added to the solution. The reaction was warmed to room temperature before being refluxed for 24 hours. The solution was cooled to room temperature and was quenched by 4.0 mL of water, 4.0 mL of 15% NaOH and an additional 12.0 mL of water. The solvent was removed in vacuo and the residue was taken up in 600 mL of refluxing ethanol. The hot solution was filtered through celite and the solvent removed in vacuo to produce a light brown solid. This compound was used in subsequent reactions without further purification. The yield of the product, 6-hydroxymethyl-2-pyridone, was 5.2729 g (58.63% Yield). Characterization data of the product was consistent with literature.

0.2021 g (1.615 mmol) of the 6-hydroxymethyl-2-pyridone was suspended in 15 mL of THF in a 100 mL RBF under the presence of argon gas and was placed in a −80° C. methanol bath. 1.03 mL (1.648 mmol) of BuLi was added dropwise to the reaction which was stirred for 20 min. 0.4374 grams (1.641 mmol) of 4-iodobenzoyl chloride was dissolved in 15 mL of THF and brought to −80° C. before being added dropwise to the reaction mixture. The reaction was allowed to stir at −80° C. for 48 hours before being warmed to room temperature. The reaction was quenched with 20 mL of water and extracted with ethyl acetate (4×20 mL), the organic layers combined and washed with brine (3×20 mL), and dried over MgSO$_4$. The solvent was removed in vacuo to produce a brown solid. The product was purified by crystallization from toluene. The yield of the reaction was 0.032 g (5.58% Yield). MP: 206-208° C. IR (cm$^{-1}$) 3426.48 (m, broad), υ (O—H), 3126.38 (m, broad), υ (N—H), 1722.45 (m), υ (C=O), 1656.57 (s), 1392.33 (m) υ (C=C aromatic). $^1$H NMR (DMSO-d$_6$, 500 MHz) δ: 5.12 (s, 2H), 6.35 (d, J=9.1 Hz, 2H), 7.45 (t, J=7.0 Hz, 1H), 7.76 (d, J=4.8 Hz, 2H), 7.94 (d, J=9.0 Hz, 2H), 11.75 (s, 1H). HRMS: m/e, found 377.9598 (M$^+$Na$^+$). Calc. for C$_{13}$H$_{10}$INO$_3$Na: 377.9603.

Example 5

(1,6-dihydro-6-oxopyridin-2-yl)methyl 4-fluorobenzoate

In Example 5, 0.2006 grams (1.60 mmole) of 6-(hydroxymethyl)pyridine-2(1H)-one was suspended in 160 mL of THF in a 250 mL round bottom flask under the presence of argon gas. Then, 0.0671 g (1.68 mmole) of 60% NaH dispersed in mineral oil was added and the solution was stirred for 20 min. 0.19 mL (1.58 mmole) of 4-fluorobenzoyl chloride was dissolved in 20 mL of THF and added dropwise into the alcohol reaction mixture at a rate of 10 μL/min. The reaction stirred for 48 hours under the presence of argon gas before being quenched with 20 mL of water. The reaction was washed with ethyl acetate (4×20 mL), the organic layers combined, washed with saturated NaHCO$_3$ (4×20 mL), washed with Brine (3×20 mL) and finally dried over MgSO$_4$. The solvent was removed in vacuo to produce a dull yellow solid. The compound was purified by column chromatography (methanol/dichloromethane). The result was a fine white powder. (0.1287 grams, 32.48% Yield). $^1$H NMR (DMSO-d$_6$, 500 MHz) δ: 5.12 (s, 2H) 6.29-6.41 (m, 2H) 7.38 (t, 2H) 7.45 (t, 1H) 8.08 (t, 2H) 11.74 (s, 1H).

Example 6

(1,6-dihydro-6-oxopyridin-2-yl)methyl 4-cyanobenzoate

In Example 6, 0.2055 grams (1.64 mmole) of 6-(hydroxymethyl)pyridine-2(1H)-one was suspended in 160 mL of THF in a 250 mL round bottom flask under the presence of argon gas. Then, 0.0672 g (1.68 mmole) of 60% NaH dispersed in mineral oil was added, and the solution was stirred for 20 min. 0.2638 g (1.59 mmole) of 4-fluorobenzoyl chloride was dissolved in 20 mL of THF and added dropwise into the alcohol reaction mixture at a rate of 10 µL/min. The reaction was stirred for 48 hours under the presence of argon gas before being quenched with 20 mL of water. The reaction was washed with ethyl acetate (4×20 mL), the organic layers combined, washed with saturated NaHCO$_3$ (4×20 mL), washed with Brine (3×20 mL) and finally dried over MgSO$_4$. The solvent was removed in vacuo to produce a dull yellow solid. The compound was purified by column chromatography (methanol/dichloromethane). The result was a fine white powder. (0.0114 grams, 2.73% Yield). $^1$H NMR (DMSO-d$_6$, 500 MHz) δ: 5.16 (s, 2H) 6.39 (m, 2 µl) 7.45 (t, 1H) 8.03 (d, 2H) 8.16 (d, 2H) 11.78 (s, 1H).

Example 7

1'-methylpiperidin-4'-yl 4-iodobenzoate

In Example 7, 1.08 g (9.38 mmol) of 4-hydroxy-1-methylpiperidine was dissolved in 50 mL of dry tetrahydrofuran (THF) to give a clear, pale brown solution in a 250 mL round bottom flask (RBF) under the presence of argon gas (99.999% purity). This solution was cooled to −78° C. in an ethyl acetate/liquid nitrogen bath and 10.5 mL of 1.6 M butyl lithium in hexanes was added drop-wise over a 10 min period. In a weigh boat, 3.9986 g (15.01 mmol) of 4-iodobenzoyl chloride was measured and then transferred to a 50 mL RBF. The 4-iodobenzoyl chloride was then dissolved in 25 mL of dry THF under the presence of argon gas and a clear, colourless solution resulted. The 4-iodobenzoyl chloride solution was then added drop-wise over a 10 min period to the 4-hydroxy-1-methylpiperidine solution. The resulting reaction mixture was slowly warmed from −78° C. to room temperature over a 2 h period with continuous stirring. The final reaction solution had a clear, dark reddish brown appearance. The reaction solution (75 mL) was removed from the argon atmosphere, quenched and washed with water (2×25 mL), and extracted with ethyl acetate (2×25 mL). The organic layer was dried over anhydrous magnesium sulfate for 30 min, filtered and concentrated to dryness under reduced pressure. The product was purified by flash chromatography on silica gel using a methanol-dichloromethane mixture (1:9, v/v) as the eluting solvent. The yield of the product was 1.8554 g (36% yield) of an off white solid. $^1$H NMR: (CDCl$_3$, 500.1 MHz) δ 7.81 (d, J=8.5 Hz, 2H), 7.75 (d, J=8.5 Hz, 2H), 5.04 (m, 1H), 2.70 (s, 2H), 2.35 (s, 2H), 2.08-2.01 (m, 2H), 1.91-1.84 (m, 2H). $^{13}$C NMR: (CDCl$_3$, 125.8 MHz) δ 166 (0), 138 (1), 131 (1), 130 (0), 100 (0), 70 (1), 53 (2), 46 (3), 31 (2). HRMS: m/e, found 345.0233±0.0008 (M$^+$). Calc. for C$_{13}$H$_{16}$INO$_2$: 345.0226. MP: 128.6-129.9° C. IR (cm$^{-1}$): (nujol) 2799, 1711, 1585, 1283, 1268, 1118.

Example 8

1'-methylpiperidin-4'-yl 4-fluorobenzoate

In Example 8, 09418 g (8.17 mmol) of 4-hydroxy-1-methylpiperidine was dissolved in 15 mL of dry THF to give a clear, pale brown solution in a 100 mL RBF under the presence of argon gas (99.999% purity). This solution was cooled to −78° C. in an ethyl acetate/liquid nitrogen bath and 5.0 mL of 1.6 M butyl lithium in hexanes was added drop-wise over a 10 min period. 0.88 mL (7.34 mmol) of 4-fluorobenzoyl chloride was then added drop-wise over a 2 min period to the 4-hydroxy-1-methylpiperidine solution. The resulting reaction mixture was slowly warmed from −78° C. to room temperature over a 13 h period with continuous stirring. The final reaction solution had a clear yellow appearance. The reaction solution (20 mL) was removed from the argon atmosphere, quenched and washed with water (2×10 mL), and extracted with ethyl acetate (2×10 mL). The organic layer was dried over anhydrous magnesium sulfate for 30 min, filtered and concentrated to dryness under reduced pressure. The product was purified by flash chromatography on silica gel using a methanol-dichloromethane mixture (1:9, v/v) as the eluting solvent. The yield of the product was 0.7204 g (42% yield) of a pale yellow solid. $^1$H NMR: (CDCl$_3$, 500.1 MHz) δ 8.07-8.05 (m, 2H), 7.11 (dd, J=8.7, 8.6 Hz, 2H), 5.05-5.03 (m, 1H), 2.68 (m, 2H), 2.33 (m, 2H), 2.32 (s, 3H), 2.00-2.04 (m, 2H), 1.84-1.89 (m, 2H). $^{13}$C NMR: (CDCl$_3$, 125.8 MHz) δ 167 (0), 165 (0), 132 (1), 127 (0), 115 (1), 70 (1), 53 (2), 46 (3), 31 (2). HRMS: m/e, found 237.1173±0.0008 (M$^+$). Calc. for C$_{13}$H$_{16}$FNO$_2$: 237.1165. MP: 47.8-48.4° C. IR (cm$^{-1}$): 2942, 2785, 1717, 1604, 1508, 1467, 1454, 1412, 1275, 1117, 1007, 854.

Example 9

1'-methylpiperidin-4'-yl 4-cyanobenzoate

In Example 9, 0.9463 g (8.22 mmol) of 4-hydroxy-1-methylpiperidine was dissolved in 15 mL of dry THF to give a clear, pale brown solution in a 100 mL RBF under the presence of argon gas (99.999% purity). This solution was cooled to −78° C. in an ethyl acetate/liquid nitrogen bath and 5.0 mL of 1.6 M butyl lithium in hexanes was added drop-wise over a 10 min period. Then, 1.2124 g (7.32 mmol) of 4-cyanobenzoyl chloride was measured into a 50 mL RBF and dissolved in 25 mL of dry THF under the presence of argon gas and a clear, colourless solution resulted. This 4-cyanobenzoyl chloride was then added drop-wise over a 2 min period to the 4-hydroxy-1-methylpiperidine solution. The resulting reaction mixture was slowly warmed from −78° C. to room temperature over a 13 h period with continuous stirring. The final reaction solution had a clear yellow appearance. The reaction solution (20 mL) was removed from the argon atmosphere, quenched and washed with water (2×10 mL), saturated sodium chloride (1×10 mL) and extracted with ethyl acetate (2×10 mL). The organic layer was dried over anhydrous magnesium sulfate for 30 min, filtered and concentrated to dryness under reduced pressure. The product was purified by flash chromatography on silica gel using a methanol-dichloromethane mixture (1:9, v/v) as the eluting solvent. The yield of the product was 1.0619 g (59% yield) of an off-white solid. $^1$H NMR: (CDCl$_3$, 500.1 MHz) δ 8.14 (d, J=8.4, 2H), 7.75 (d, J=8.5, 2H), 5.08-5.05 (m, 1H), 2.69 (s, 2H), 2.33 (s, 2H), 2.32 (s, 3H), 2.06-2.02 (m, 2H), 1.91-1.84 (m, 2H). $^{13}$C NMR: (CDCl$_3$, 125.8 MHz) δ 164 (0), 134 (0), 132 (1), 130 (1), 118 (0), 116 (0), 71 (1), 53 (2), 46 (3), 31 (2). HRMS: m/e, found 244.1216±0.0008 (M$^+$). Calc. for C$_{14}$H$_{16}$N$_2$O$_2$: 244.1212. MP: 119.8-120.4° C. IR (cm$^{-1}$): (nujol) 2795, 2228, 1718, 1278, 1122, 1030.

Example 10

1'-methylpiperidin-4'-yl benzoate

In Example 10, 0.6791 g (5.89 mmol) of 4-hydroxy-1-methylpiperidine was dissolved in 20 mL of dry THF to give a clear, pale brown solution in a 100 mL RBF under the presence of argon gas (99.999% purity). This solution was cooled to −78° C. in an ethyl acetate/liquid nitrogen bath, and 3.8 mL of 1.6 M butyl lithium in hexanes was added drop-wise over a 10 min period. Then, 0.62 mL (5.35 mmol) of benzoyl chloride was added drop-wise over a 2 min period to the 4-hydroxy-1-methylpiperidine solution. The resulting reaction mixture was slowly warmed from −78° C. to room temperature over an 18 h period with continuous stirring. The final reaction solution had a clear yellow appearance. The reaction solution (20 mL) was removed from the argon atmosphere, quenched and washed with water (2×20 mL) and extracted with ethyl acetate (2×10 mL). The organic layer was dried over anhydrous magnesium sulfate for 30 min, filtered and concentrated to dryness under reduced pressure. The product was purified by flash chromatography on silica gel using a methanol-dichloromethane mixture (1:9, v/v) as the eluting solvent. The yield of the product was 0.5987 g (51% yield) of a clear, pale yellow oil. $^1$H NMR: (500.1 MHz) δ 8.06 (d, J=7.0 Hz, 2H), 7.57 (tt, J=1.3, J=7.5, 1H), 7.45 (t, J=7.9, 2H), 5.06-5.08 (m, 1H), 2.70 (s, 2H), 2.34 (s, 2H), 2.33 (s, 3H) 2.01-2.06 (m, 2H), 1.85-1.92 (m, 2H). $^{13}$C NMR: (128.5 MHz) δ 166 (0), 133 (1), 130 (0), 130 (1), 128 (1), 53 (2), 46 (3), 31 (2). MP: liquid. IR (cm$^{-1}$): (neat) 3410, 2942, 2792, 1717, 1602, 1585, 1451, 1275, 1112, 1035, 713.

Example 11

1'-methylpiperidin-4'-yl 3-iodobenzoate

In Example 11, 3-iodobenzoyl chloride was synthesized from 1.8081 g (7.29 mmol) of 3-iodobenzoic acid dissolved in 1.60 mL of thionyl chloride in a 100 mL RBF. This solution was refluxed for 2 h and monitored by TLC. The thionyl chloride was removed under reduced pressure and a pale yellow solid was obtained. 0.9835 g (8.54 mmol) of 4-hydroxy-1-methylpiperidine was dissolved in 15 mL of dry THF to give a clear, pale brown solution in a 100 mL RBF under the presence of argon gas (99.999% purity). This solution was cooled to −78° C. in an ethyl acetate/liquid nitrogen bath and 5.0 mL of 1.6 M butyl lithium in hexanes was added drop-wise over a 10 min period. The pale yellow solid, 3-iodobenzoyl chloride, was dissolved in 20 mL of dry THF under the presence of argon gas and a clear, colourless solution resulted. This 3-iodobenzoyl chloride was then added drop-wise over a 2 min period to the 4-hydroxy-1-methylpiperidine solution. The resulting reaction mixture was slowly warmed from −78° C. to room temperature over a 13 h period with continuous stirring. The final reaction solution had a clear yellow appearance. The reaction solution (40 mL) was removed from the argon atmosphere, quenched and washed with water (2×15 mL), saturated sodium chloride (1×15 mL) and extracted with ethyl acetate (2×15 mL). The organic layer was dried over anhydrous magnesium sulfate for 30 min, filtered and concentrated to dryness under reduced pressure. The product was purified by flash chromatography on silica gel using a methanol-dichloromethane mixture (1:9, v/v) as the eluting solvent. The yield of the product was 1.3831 g (55% yield) of an off-white solid. $^1$H NMR: (CDCl$_3$, 500.1 MHz) δ 8.36 (s, 1H), 8.01 (d, J=7.8, 1H), 7.89 (d, J=7.9, 1H), 7.19 (t, J=7.8, 1H), 5.04 (s, 1H), 2.71 (s, 2H), 2.33 (m, 5H), 2.05-2.02 (m, 2H), 1.91-1.85 (m, 2H). $^{13}$C NMR: (CDCl$_3$, 125.8 MHz) δ 164 (0), 142 (1), 138 (1), 133 (0), 130 (1), 129 (1), 94 (0), 71 (1), 53 (2), 46 (3), 31 (2). HRMS: m/e, found 346.0298±0.0008 (M$^+$). Calc. for C$_{13}$H$_{16}$IN$_1$O$_2$: 345.0226. MP: 67.9-68.2° C. IR (cm$^{-1}$): (nujol) 2735, 1725, 1567, 1323, 1276, 1254, 1120.

Example 12

1'-methylpiperidin-4'-yl 3-fluorobenzoate

In Example 12, 0.9400 g (8.16 mmol) of 4-hydroxy-1-methylpiperidine was dissolved in 15 mL of dry THF to give a clear, pale brown solution in a 100 mL RBF under the presence of argon gas (99.999% purity). This solution was cooled to −78° C. in an ethyl acetate/liquid nitrogen bath and 5.0 mL of 1.6 M butyl lithium in hexanes was added drop-wise over a 10 min period. Then, 0.90 mL (7.50 mmol) of 3-fluorobenzoyl chloride was added drop-wise over a 2 min period to the 4-hydroxy-1-methylpiperidine solution. The resulting reaction mixture was slowly warmed from −78° C. to room temperature over a 13 h period with continuous stirring. The final reaction solution had a clear yellow appearance. The reaction solution (20 mL) was removed from the argon atmosphere, quenched and washed with water (2×10 mL), saturated sodium chloride (1×10 mL) and extracted with ethyl acetate (2×10 mL). The organic layer was dried over anhydrous magnesium sulfate for 30 min, filtered and concentrated to dryness under reduced pressure. The product was purified by flash chromatography on silica gel using a methanol-dichloromethane mixture (1:9, v/v) as the eluting solvent. The yield of the product was 1.2045 g (69% yield) of whitish solid. $^1$H NMR: (CDCl$_3$, 500.1 MHz) δ 7.85-7.83 (m, 1H), 7.73-7.71 (m, 1H), 7.44-7.41 (m, 1H), 7.28-7.24 (m, 1H), 5.07-5.04 (m, 1H), 2.69 (s, 2H), 2.35 (s, 2H), 2.32 (s, 3H), 2.06-2.00 (m, 2H), 1.91-1.84 (m, 2H). $^{13}$C NMR: (CDCl$_3$, 125.8 MHz) δ 165 (0), 164 (d, J=247.03) (0), 133 (d, J=7.30) (0), 130 (d, J=7.71) (1), 125 (1), 120 (d, J=21.34) (1), 116 (d, J=22.94) (1), 71 (1), 53 (2), 46 (3), 31 (2). HRMS: m/e, found 238.1234±0.0008 (M$^+$H$^+$). Calc. for C$_{13}$H$_{16}$FNO$_2$+H, 238.1244. MP: liquid. IR (cm$^{-1}$): (neat) 2943, 2786, 1717, 1487, 1468, 1279, 1205, 757.

Example 13

1'-methylpiperidin-4'-yl 3-cyanobenzoate

In Example 13, 0.9764 g (8.48 mmol) of 4-hydroxy-1-methylpiperidine was dissolved in 15 mL of dry THF to give a clear, pale brown solution in a 100 mL RBF under the presence of argon gas (99.999% purity). This solution was cooled to −78° C. in an ethyl acetate/liquid nitrogen bath and 5.0 mL of 1.6 M butyl lithium in hexanes was added drop-wise over a 10 min period. Then, 1.2016 g (7.26 mmol) of 3-cyanobenzoyl chloride was measured into a 50 mL RBF and dissolved in 15 mL of dry THF under the presence of argon gas and a clear, colourless solution resulted. This 3-cyanobenzoyl chloride was then added drop-wise over a 2 min period to the 4-hydroxy-1-methylpiperidine solution. The resulting reaction mixture was slowly warmed from −78° C. to room temperature over a 13 h period with continuous stirring. The final reaction solution had a clear yellow appearance. The reaction solution (35 mL) was removed from the argon atmosphere, quenched and washed with water (2×15 mL), saturated sodium chloride (1×15 mL) and extracted with ethyl acetate (2×15 mL). The organic layer was dried over anhydrous magnesium sulfate for 30 min, filtered and concentrated to dryness under reduced pressure. The product was purified by flash chromatography on silica gel using a methanol-dichloromethane mixture (1:9, v/v) as the eluting solvent. The yield of the product was 1.2844 g (77% yield) of an off-white solid. $^1$H NMR: (CDCl$_3$, 500.1 MHz) δ 8.36 (d, J=1.3, 1H), 8.31 (dt, J=7.9 Hz, J=1.2 Hz 1H), 7.88 (dd, J=7.7, J=1.2, 1H), 7.63 (t, J=7.8, 1H), 5.10-5.13 (m, 1H), 2.74 (s, 2H), 2.40 (s, 2H), 2.37 (s, 3H), 2.07-2.10 (m, 2H), 1.89-1.95 (m, 2H). $^{13}$C NMR: (CDCl$_3$, 125.8 MHz) 163 (0), 136 (1), 134 (1), 133 (1), 132 (0), 129 (1), 118 (0), 113 (0), 53 (2), 46 (3), 31 (2). HRMS: m/e, found 244.1221±0.0008 (M$^+$). Calc. for C$_{14}$H$_{16}$N$_2$O$_2$: 244.1212. MP: 73.1-74.0° C. IR (cm$^{-1}$): (nujol) 2786, 2235, 1720, 1604, 1278, 1188, 1033, 757.

Example 14

(S)-1'-methylpyrrolidin-3'-yl 4-iodobenzoate

In Example 14, 0.257 mL (2.52 mmol) of (S)-(+)-1-methyl-3-pyrrolidinol was dissolved in 10 mL of dry THF to give a clear, pale brown solution in a 50 mL RBF under the presence of argon gas (99.999% purity). This solution was cooled to −78° C. in an ethyl acetate/liquid nitrogen bath and 1.60 mL of 1.6 M butyl lithium in hexanes was added drop-wise over a 10 min period. Then, 0.5870 g (2.20 mmol) of 4-iodobenzoyl chloride was measured into a 50 mL RBF and dissolved in 10 mL of dry THF under the presence of argon gas; a clear, pale yellow solution resulted. This 4-iodobenzoyl chloride solution was then added drop-wise over a 2 min period to the (S)-(+)-1-methyl-3-pyrrolidinol solution. The resulting reaction mixture was slowly warmed from −78° C. to room temperature over a 3 h period with continuous stirring. The final reaction solution had a clear yellow appearance. The reaction solution (20 mL) was removed from the argon atmosphere, quenched and washed with water (2×10 mL), saturated sodium chloride (2×15 mL) and extracted with ethyl acetate (2×10 mL). The organic layer was dried over anhydrous magnesium sulfate for 30 min, filtered and concentrated to dryness under reduced pressure. The product was purified by flash chromatography on silica gel using a methanol-dichloromethane mixture (1:9, v/v) as the eluting solvent. The yield of the product was 0.3053 g (36% yield) of pale yellow solid. $^1$H NMR: (500.1 MHz) δ 7.79 (dt, J=2.0, J=8.7, 2H), 7.75 (dt, J=2.0, J=8.7, 2H), 5.40-5.43 (m, 1H), 2.85-2.88 (m, 1H), 2.83 (d, J=2.6, 1H), 2.77-2.81 (m, 1H), 2.37-2.42 (m, 5H), 1.99-2.03 (m, 1H). $^{13}$C NMR: (128.5 MHz) δ 166 (0), 138 (1), 131 (1), 130 (0), 101 (0), 76 (1), 62 (2), 55 (2), 42 (3), 33 (2). MP: 68.7-70.4° C. IR (cm$^{-1}$): (nujol) 2776, 1724, 1586, 1333, 1268, 1197, 1147, 1115, 1103, 1008, 754.

Example 15

(S)-1'-methylpyrrolidin-3'-yl-4-cyanobenzoate

In Example 15, 0.260 mL (2.55 mmol) of (S)-(+)-1-methyl-3-pyrrolidinol was dissolved in 10 mL of dry THF to give a clear, pale brown solution in a 50 mL RBF under the presence of argon gas (99.999% purity). This solution was cooled to −78° C. in an ethyl acetate/liquid nitrogen bath and 1.60 mL of 1.6 M butyl lithium in hexanes was added drop-wise over a 10 min period. Then, 0.3705 g (2.24 mmol) of 4-cyanobenzoyl chloride was measured into a 50 mL RBF and dissolved in 10 mL of dry THF under the presence of argon gas and a clear, pale yellow solution resulted. This 4-cyanobenzoyl chloride solution was then added drop-wise over a 2 min period to the (S)-(+)-1-methyl-3-pyrrolidinol solution. The resulting reaction mixture was slowly warmed from −78° C. to room temperature over a 14 h period with continuous stirring. The final reaction solution had a clear yellow appearance. The reaction solution (20 mL) was removed from the argon atmosphere, quenched and washed with water (2×10 mL), saturated sodium chloride (2×20 mL) and extracted with ethyl acetate (2×20 mL). The organic layer was dried over anhydrous magnesium sulfate for 30 min, filtered and concentrated to dryness under reduced pressure. The product was purified by flash chromatography on silica gel using a methanol-dichloromethane mixture (1:9, v/v) as the eluting solvent. The yield of the product was 0.1541 g (27% yield) of brownish yellow solid. $^1$H NMR: (500.1 MHz) δ 8.15 (dt, J=1.4, J=8.7, 2H), 7.74 (dt, J=1.4, J=8.6, 2H), 5.43-5.46 (m, 1H), 2.87-2.91 (m, 2H), 2.77-2.80 (m, 1H), 2.37-2.42 (m, 5H), 2.01-2.06 (m, 1H). $^{13}$C NMR: (128.5 MHz) δ 165 (0), 134 (0), 132 (1), 130 (1), 118 (0), 116 (0), 77 (1), 62 (2), 55 (2), 42 (3), 33 (2). MP: 54.5-56.0° C. IR (cm$^{-1}$): (nujol) 2776, 2228, 1717, 1329, 1299, 1275, 1178, 1146, 1109, 768.

Example 16

R-1'-methylpyrrolidin-3'-yl 4-iodobenzoate

In Example 16, 0.260 mL (2.55 mmol) of R-(−)-1-methyl-3-pyrrolidinol was dissolved in 10 mL of dry THF to give a clear, pale brown solution in a 50 mL RBF under the presence of argon gas (99.999% purity). This solution was cooled to −78° C. in an ethyl acetate/liquid nitrogen bath and 1.60 mL of 1.6 M butyl lithium in hexanes was added drop-wise over a 10 min period. Then, 0.5932 g (2.23 mmol) of 4-iodobenzoyl chloride was measured into a 50 mL RBF and dissolved in 10 mL of dry THF under the presence of argon gas and a clear, pale yellow solution resulted. This 4-iodobenzoyl chloride solution was then added drop-wise over a 2 min period to the R-(−)-1-methyl-3-pyrrolidinol solution. The resulting reaction mixture was slowly warmed from −78° C. to room temperature over a 3 h period with continuous stirring. The final reaction solution had a clear yellow appearance. The reaction solution (20 mL) was removed from the argon atmosphere, quenched and washed with water (2×15 mL), saturated sodium chloride (2×15 mL) and extracted with ethyl acetate (2×20 mL). The organic layer was dried over anhydrous magnesium sulfate for 30 min, filtered and concentrated to dryness under reduced pressure. The product was purified by flash chromatography on silica gel using a methanol-dichloromethane mixture (1:9, v/v) as the eluting solvent. The yield of the product was 0.3696 g (47% yield) of brownish yellow solid. $^1$H NMR: (500.1 MHz) δ 7.80 (dt, J=1.7, J=8.6, 2H), 7.76 (dt, J=1.9, J=8.5, 2H), 5.31-5.43 (m, 1H), 2.84-2.88 (m, 1H), 2.83 (d, J=2.6, 1H), 2.77-2.81 (m, 1H), 2.37-2.42 (m, 5H), 2.00-2.03 (m, 1H). $^{13}$C NMR: (128.5 MHz) δ 166 (0), 138 (1), 131 (1), 130 (0), 101 (0), 76 (1), 62 (2), 55 (2), 42 (3), 33 (2). MP: 68.7-70.1° C. IR (cm$^{-1}$): (nujol) 2793, 1724, 1586, 1333, 1268, 1114, 1103, 1008, 844, 754

Example 17

R-1'-methylpyrrolidin-3'-yl-4-cyanobenzoate

In Example 17, 0.270 mL (2.46 mmol) of R-(−)-1-methyl-3-pyrrolidinol was dissolved in 10 mL of dry THF to give a clear, pale brown solution in a 50 mL RBF under the presence of argon gas (99.999% purity). This solution was cooled to −78° C. in an ethyl acetate/liquid nitrogen bath and 1.60 mL of 1.6 M butyl lithium in hexanes was added drop-wise over a 10 min period. Then, 0.3740 g (2.26 mmol) of 4-cyanobenzoyl chloride was measured into a 50 mL RBF and dissolved in 10 mL of dry THF under the presence of argon gas and a clear, pale yellow solution resulted. This 4-cyanobenzoyl chloride solution was then added drop-wise over a 2 min period to the R-(−)-1-methyl-3-pyrrolidinol solution. The resulting reaction mixture was slowly warmed from −78° C.

to room temperature over an 18 h period with continuous stirring. The final reaction solution had a clear yellow appearance. The reaction solution (20 mL) was removed from the argon atmosphere, quenched and washed with water (2×20 mL), saturated sodium chloride (2×20 mL) and extracted with ethyl acetate (2×20 mL). The organic layer was dried over anhydrous magnesium sulfate for 30 min, filtered and concentrated to dryness under reduced pressure. The product was purified by flash chromatography on silica gel using a methanol-dichloromethane mixture (1:9, v/v) as the eluting solvent. The yield of the product was 0.3696 g (47% yield) of brownish yellow solid. $^1$H NMR: (500.1 MHz) δ 8.16 (dt, J=1.9, J=8.7, 2H), 7.74 (dt, J=2.0, J=8.7, 2H), 5.43-5.46 (m, 1H), 2.87-2.92 (m, 2H), 2.77-2.81 (m, 1H), 2.37-2.44 (m, 5H), 2.01-2.06 (m, 1H). $^{13}$C NMR: (128.5 MHz) δ 165 (0), 134 (0), 132 (1), 130 (1), 118 (0), 116 (0), 77 (1), 62 (2), 55 (2), 42 (3), 33 (2). MP: 58.2-59.6° C. IR (cm$^{-1}$): (nujol) 2776, 2228, 1728, 1298, 1274, 1108, 860, 768.

Example 18

(6-oxo-1,6-dihydropyridin-2-yl)methyl 4-(tributylstannyl)benzoate (Formula V)

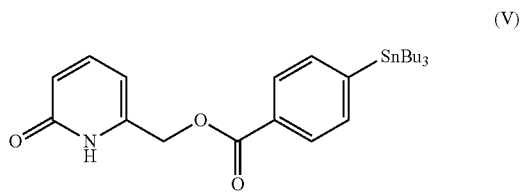

In Example 18, 0.1034 g (0.29 mmol) of (6-oxo-1,6-dihydropyridin-2-yl)methyl 4-iodobenzoate and 0.0100 g (0.008 mmol) of tetrakis(triphenylphosphine)palladium(0) were combined in a 250 mL flask, flushed under argon gas and 160 mL of toluene was added to this mixture. Then, 0.33 mL (0.66 mmol) of hexabutylditin was dissolved in 20 mL of toluene and added. The reaction was refluxed for 48 hours in the dark and the solvent removed under reduced pressure. The crude oil was purified by flash chromatography through silica gel (4:1 ethyl acetate/hexanes) to give 0.0611 g (39.41%) of (6-oxo-1,6-dihydropyridin-2-yl)methyl 4-(tributylstannyl) benzoate as a yellow oil that solidified upon standing. $^1$H NMR: 500 MHz, DMSO: 0.84 (t, J=7.4, 9H), 1.08 (t, J=8.0, 6H), 1.28 (hex, J=7.4, 6H), 1.50 (quin, J=7.4, 6H), 5.11 (s, 2H), 6.33 (d, J=8.9 Hz, 2H), 7.45 (t, J=7.1 Hz, 1H), 7.76 (d, J=8.0 Hz, 2H), 7.94 (d, J=8.0 Hz, 2H), 11.75 (s, 1H).

Example 19

(S)-1-methylpyrrolidin-3-yl 4-(tributylstannyl)benzoate

In Example 19, 0.1001 g (0.3022 mmol) of (S)-1-methylpyrrolidin-3-yl 4-iodobenzoate was dissolved in 30 mL of dry, degassed toluene and 0.355 mL (0.709 mmol) of hexabutylditin was added. Then, 0.0107 g (0.0092 mmol) of tetrakis (triphenylphosphine)palladium was dissolved in 15 mL of dry toluene and added slowly to the reaction. The resulting solution was refluxed for 20 hours before solvent removal under reduced pressure. The resulting crude product was purified by column chromatography (40:55:5, EtOAc/hexanes/triethylamine) to yield 0.1157 g (77.44%) of (S)-1-methylpyrrolidin-3-yl 4-(tributylstannyl)benzoate as a yellow oil. IR: (Neat) 2956.36, 2926.72, 2870.90, 2851.70, 2777.37, 1717.00, 1463.25, 1385.59, 1376.77, 1329.28, 1275.22, 1184.43, 1152.79, 1115.80, 1104.77, 1063.02, 1017.84, 752.43, 698.15. $^1$H NMR: (500 MHz, DMSO) 0.85 (t, J=7.5 Hz, 9H), 1.08 (m, 6H), 1.28 (sex, J=7.4 Hz, 6H), 1.51 (quin, J=7.3 Hz, 6H), 1.85 (m, 1H), 2.26 (s, 3H), 2.31 (m, 4H), 2.66 (m, 1H), 2.71, (m, 2H), 5.26, (m, 1H), 7.56 (d, J=7.9 Hz, 2H), 7.82 (d, J=7.9 Hz, 2H). $^{13}$C NMR: (126 MHz, DMSO) 9 (2), 13 (3), 27 (2), 28 (2), 32 (2), 42 (3), 54 (2), 62 (2), 75 (1), 128 (1), 129 (0), 136 (1), 149 (0), 166 (0).

Example 20

1-methylpiperidin-4-yl 4-(tributylstannyl)benzoate

In Example 20, 0.1660 g (0.4810 mmol) of 1-methylpiperidin-4-ol was dissolved in 40 mL of toluene under an atmosphere of argon gas. 0.60 mL of hexabutylditin (1.198 mmol) was added to the reaction followed by a solution containing 0.0303 g (0.0262 mmol) of Pd(PPh)$_3$ dissolved in 15 mL of toluene. The resulting solution was refluxed for 20 hours before returning to room temperature and concentrated under reduced pressure. The product was purified by column chromatography (15:1 toluene/Et$_3$N) to yield 0.1795 g (73.3%) as a yellow oil. IR: (Neat) 2955.22, 2927.08, 2870.78, 2850.71, 2783.22, 1717.21, 1463.88, 1385.44, 1274.77, 1185.45, 1116.24, 1104.37, 1093.56, 1063.12, 1039.33, 1017.61, 751.95, 697.78 cm$^{-1}$. $^1$H NMR: (500 MHz, CDCl$_3$) 0.92 (t, J=7.3 Hz, 9H), 1.12 (p, J=6.3 Hz, 6H), 1.36 (s, J=7.4 Hz, 6H), 1.57 (p, J=7.6 Hz, 6H), 1.89-1.94 (m, 2H), 2.03-2.08 (m, 2H), 2.36 (s, 5H), 2.39 (s, 2H), 2.72 (s, 2H), 5.09-5.10 (m, 1H), 7.59 (d, J=8.1 Hz, 2H), 8.00 (d, J=8.1 Hz, 2H). $^{13}$C NMR: (128 MHz, CDCl$_3$) 10, 13, 27, 29, 33, 42, 53, 128, 130, 136, 149, 166. EI-MS (m/z): 41, 55, 82, 96, 170, 198, 241, 340, 396, 452, 509. HRMS (EI) MH$^+$ (found): 510.2389±0.0008 (calculated) 510.2316.

Example 21

(6-oxo-1,6-dihydropyridin-2-yl)methyl 4-$^{123}$iodobenzoate (Formula VI)

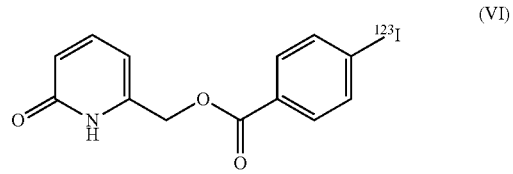 [SMILES: O=C(OCc1cccc(=O)[nH]1)c1ccc([123I])cc1]

To a solution of Na$^{123}$I (6 mCi in 0.1 N NaOH, 30 μL), 100 μL of MeOH was added. 6 (7×10$^{-6}$ mol) of HCl in water was added, the solution was mixed and briefly centrifuged. After 4 min, 50 μL (3.8590×10$^{-7}$ mol) of (6-oxo-1,6-dihydropyridin-2-yl)methyl 4-(tributylstannyl)benzoate (Example 18) in MeOH was added and the reaction mixed. 284 (8.3877×10$^{-8}$ mol) of N-chlorosuccinimide was added and the solution mixed. After 15 min, the reaction was purified and collected by HPLC (Zorbax eclipse XDB-C18 column, 4.6×250 mm, 5 μm). (6-oxo-1,6-dihydropyridin-2-yl)methyl 4-[123I]iodobenzoate eluted between 8.3 and 10.3 min using 80% MeOH—20% H$_2$O as eluent (1 mL/min). The solvent was removed under a stream of N$_2$ gas and the resulting solid was

Example 22

Methyl 1-methyl-6-oxo-1,6-dihydropyridine-2-carboxylate (Formula VII)

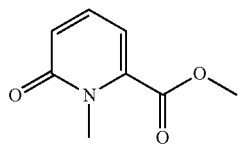

(VII)

In Example 22, 0.4006 g (2.611 mmol) of methyl 6-oxo-1,6-dihydropyridine-2-carboxylate and 0.4006 g (2.899 mmol) of potassium carbonate were combined in a 25 mL RBF. 1 mL of DMSO followed by 4 mL (64.25 mmol) of methyl iodide was added and the reaction refluxed for 4 hours. The solvent was removed under reduced pressure and the resulting oil was extracted with hot hexanes (8×25 mL), the extracts were combined and solvent removed to yield a yellow oil. Recrystallization from hexanes yielded the product as white/yellow crystals (0.1245 g, 28.52%). Melting Point: 56-57° C. IR: (Nujol) 3437.61, 1731.13, 1652.94, 1590.77, 1457.45, 1443.48, 1379.43, 1265.53, 1218.08, 1156.78, 1086.06, 900.89, 825.45, 817.06, 765.03, 755.48, 722.85 cm$^{-1}$. $^1$H NMR: (500 MHz, CDCl$_3$) 3.67 (s, 3H), 3.91 (s, 3H), 6.71 (dd, J=1.2, 9.1 Hz, 1H), 6.74 (dd, J=1.2, 6.8 Hz, 1H), 7.29 (dd, J=6.7, 9.1 Hz, 1H). $^{13}$C NMR: (126 MHz, CDCl$_3$) 33.40, 52.90, 110.42, 124.46, 137.21, 138.21, 162.45, 162.70.

This compound can be used to generate N-methyl-substituted pyridone ligands by a synthetic methodology described above, i.e. reduction to the alcohol, followed by esterification with an acid chloride. Other N-substitutions using, as a non-limiting example, moieties of R$_2$ in Formula I could be had by analogously synthesizing ethyl 1-methyl-6-oxo-1,6-dihydropyridine-2-carboxylate, propyl 1-methyl-6-oxo-1,6-dihydropyridine-2-carboxylate, hexyl 1-methyl-6-oxo-1,6-dihydropyridine-2-carboxylate, phenyl 1-methyl-6-oxo-1,6-dihydropyridine-2-carboxylate, etc.

Examples 23-28

Acetylcholinesterase In Vitro Assay

In Examples 23-28, the interaction of the ligands with AChE was determined by measuring the rate of hydrolysis of the ligand in a buffered solution containing the enzyme. AChE stock solution consisted of 240 μg of human recombinant AChE dissolved in 1.5 mL of 0.1% aq. Gelatin. All ligands used in the assay were dissolved in a minimal amount of acetonitrile to form a ligand solution. 0.1 M Phosphate buffer PH 8.0 consisted of 1.2 g of NaH$_2$PO$_4$ dissolved in 100 mL of water and adjusted to the appropriate pH. The Assay was carried out by mixing 0.1 μmole of ligand solution with 5 μL of AChE stock solution and bringing the volume in a quartz cuvette of 1 cm path length to 1.5 mL with phosphate buffer. Scans using an UltraSpec 2100 Pro UV/Visible spectrophotometer over a wavelength of 200-900 nm monitored the rate of hydrolysis of the ligand by the enzyme. Change of absorbance in the spectrum indicated hydrolysis of the ligand by the enzyme.

Example 23

AChE Analysis of (1,2 dihydro-2-oxopyridin-3-yl)methyl 4-iodobenzoate

In Example 23, 3.5 mg of (1,2 dihydro-2-oxopyridin-3-yl) methyl 4-iodobenzoate was dissolved in 20 mL of acetonitrile. 100 μL of this solution was placed in a quartz cuvette of 1 cm path length and 1.40 mL of phosphate buffer pH 8.0 was added. The reaction was commenced with the addition of 5 μL of AChE stock solution. The absorbance was scanned over a range of 200-900 nm every 2 min for a total of 30 min. The results of this experiment generally indicate that enzymatic hydrolysis of the compounds does not occur in the presence of AChE.

Example 24

AChE Analysis of (1,2-dihydro-2-oxopyridin-3-yl)methyl 4-fluorobenzoate

In Example 24, 6.5 mg of (1,2-dihydro-2-oxopyridin-3-yl) methyl 4-fluorobenzoate was dissolved in 10 mL of acetonitrile. 100 μL of this solution was placed in a quartz cuvette of 1 cm path length and 1.40 mL of phosphate buffer pH 8.0 was added. The reaction was commenced with the addition of 5 μL of AChE stock solution. The absorbance was scanned over a range of 200-900 nm every 1 min for a total of 20 min. The results of this experiment generally indicate that enzymatic hydrolysis of the compounds does not occur in the presence of AChE.

Example 25

AChE Analysis of (1,2-dihydro-2-oxopyridin-3-yl)methyl 4-cyanobenzoate

In Example 25, 2.5 mg of (1,2 dihydro-2-oxopyridin-3-yl) methyl 4-cyanobenzoate was dissolved in 15 mL of acetonitrile. 100 μL of this solution was placed in a quartz cuvette of 1 cm path length and 1.40 mL of phosphate buffer pH 8.0 was added. The reaction was commenced with the addition of 5 μL of AChE stock solution. The absorbance was scanned over a range of 200-900 nm every 1 min for a total of 20 min. The results of this experiment generally indicate that enzymatic hydrolysis of the compounds does not occur in the presence of AChE.

Example 26

AChE Analysis of (1,6-dihydro-6-oxopyridin-2-yl)methyl 4-iodobenzoate

In Example 26, 3.5 mg of (1,6 dihydro-6-oxopyridin-2-yl) methyl 4-iodobenzoate was dissolved in 20 mL of acetonitrile. 100 μL of this solution was placed in a quartz cuvette of 1 cm path length and 1.40 mL of phosphate buffer pH 8.0 was added. The reaction was commenced with the addition of 5 μL of AChE stock solution. The absorbance was scanned over a range of 200-900 nm every 1 min for a total of 20 min. The results of this experiment generally indicate that enzymatic hydrolysis of the compounds does not occur in the presence of AChE.

Example 27

AChE Analysis of (1,6-dihydro-6-oxopyridin-2-yl)methyl 4-fluorobenzoate

In Example 27, 2.7 mg of (1,6 dihydro-6-oxopyridin-2-yl)methyl 4-fluorobenzoate was dissolved in 10 mL of acetonitrile. 100 µL of this solution was placed in a quartz cuvette of 1 cm path length and 1.40 mL of phosphate buffer pH 8.0 was added. The reaction was commenced with the addition of 5 µL of AChE stock solution. The absorbance was scanned over a range of 200-900 nm every 30 sec for a total of 5.5 min. The results of this experiment generally indicate that enzymatic hydrolysis of the compounds does not occur in the presence of AChE.

Example 28

AChE Analysis of (1,6-dihydro-6-oxopyridin-2-yl)methyl 4-cyanobenzoate

In Example 28, 2.5 mg of (1,6 dihydro-6-oxopyridin-2-yl)methyl 4-cyanobenzoate was dissolved in 8 mL of acetonitrile. 100 µL of this solution was placed in a quartz cuvette of 1 cm path length and 1.40 mL of phosphate buffer pH 8.0 was added. The reaction was commenced with the addition of 5 µL of AChE stock solution. The absorbance was scanned over a range of 200-900 nm every 30 sec for a total of 7.5 min. The results of this experiment generally indicate that enzymatic hydrolysis of the compounds does not occur in the presence of AChE.

Example 29

AChE Analysis of 1'-methylpiperidin-4'-yl 4-iodobenzoate

In Example 29, 1.8 mg of 1'-methylpiperidin-4'-yl-4-iodobenzoate was dissolved in 2 mL of 50% acetonitrile/water. 50 µL of this solution was placed in a quartz cuvette of 1 cm path length and 1.45 mL of phosphate buffer pH 8.0 was added. The reaction was commenced with the addition of 15 µL of AChE stock solution. The absorbance was scanned over a range of 200-300 nm every 2 min for a total of 30 min. The results of this experiment generally indicate that enzymatic hydrolysis of the compounds does not occur in the presence of AChE.

Example 30

AChE Analysis of 1'-methylpiperidin-4'-yl 4-fluorobenzoate

In Example 30, 2.4 mg of 1'-methylpiperidin-4'-yl-4-fluorobenzoate was dissolved in 2 mL of 50% acetonitrile/water. 50 µL of this solution was placed in a quartz cuvette of 1 cm path length and 1.45 mL of phosphate buffer pH 8.0 was added. The reaction was commenced with the addition of 15 µL of AChE stock solution. The absorbance was scanned over a range of 200-300 nm every 2 min for a total of 30 min. The results of this experiment generally indicate that enzymatic hydrolysis of the compounds does not occur in the presence of AChE.

Example 31

AChE Analysis of 1'-methylpiperidin-4'-yl-4-cyanobenzoate

In Example 31, 2.4 mg of 1'-methylpiperidin-4'-yl 4-cyanobenzoate was dissolved in 2 mL of 50% acetonitrile/water. 50 µL of this solution was placed in a quartz cuvette of 1 cm path length and 1.45 mL of phosphate buffer pH 8.0 was added. The reaction was commenced with the addition of 15 µL of AChE stock solution. The absorbance was scanned over a range of 200-300 nm every 2 min for a total of 30 min. The results of this experiment generally indicate that enzymatic hydrolysis of the compounds does not occur in the presence of AChE.

Example 32

AChE Analysis of 1'-methylpiperidin-4'-yl benzoate

In Example 32, 2.2 mg of 1'-methylpiperidin-4'-yl benzoate was dissolved in 2 mL of 50% acetonitrile/water. 50 µL of this solution was placed in a quartz cuvette of 1 cm path length and 1.45 mL of phosphate buffer pH 8.0 was added. The reaction was commenced with the addition of 15 µL of AChE stock solution. The absorbance was scanned over a range of 200-300 nm every 2 min for a total of 30 min. The results of this experiment generally indicate that enzymatic hydrolysis of the compounds does not occur in the presence of AChE.

Example 33

AChE Analysis of 1'-methylpiperidin-4'-yl 3-iodobenzoate

In Example 33, 0.35 mg of 1'-methylpiperidin-4'-yl 3-iodobenzoate was dissolved in 2 mL of 50% acetonitrile/water. 50 µL of this solution was placed in a quartz cuvette of 1 cm path length and 1.45 mL of phosphate buffer pH 8.0 was added. The reaction was commenced with the addition of 15 µL of AChE working concentration. The absorbance was scanned over a range of 200-300 nm every 2 min for a total of 30 min. The results of this experiment generally indicate that enzymatic hydrolysis of the compounds does not occur in the presence of AChE.

Example 34

AChE Analysis of 1'-methylpiperidin-4'-yl 3-cyanobenzoate

In Example 34, 1'-methylpiperidin-4'-yl 3-cyanobenzoate was tested according to the process described above in Example 23. The results of this experiment generally indicate that enzymatic hydrolysis of the compounds does not occur in the presence of AChE.

Example 35

AChE Analysis of (S)-1'-methylpyrrolidin-3'-yl 4-iodobenzoate

In Example 35, 3.2 mg of 1'-methylpiperidin-3'-yl 4-iodobenzoate was dissolved in 2 mL of 50% acetonitrile/water. 50

μL of this solution was placed in a quartz cuvette of 1 cm path length and 1.45 mL of phosphate buffer pH 8.0 was added. The reaction was commenced with the addition of 15 μL of AChE stock solution. The absorbance was scanned over a range of 200-300 nm every 2 min for a total of 30 min. The results of this experiment generally indicate that enzymatic hydrolysis of the compounds does not occur in the presence of AChE.

Example 36

AChE Analysis of (S)-1'-methylpyrrolidin-3'-yl 4-cyanobenzoate

In Example 36, 2.3 mg of (S)-1'-methylpyrrolidin-3'-yl 4-cyanobenzoate was dissolved in 2 mL of 50% acetonitrile/water. 50 μL of this solution was placed in a quartz cuvette of 1 cm path length and 1.45 mL of phosphate buffer pH 8.0 was added. The reaction was commenced with the addition of 15 μL of AChE stock solution. The absorbance was scanned over a range of 200-300 nm every 2 min for a total of 30 min. The results of this experiment generally indicate that enzymatic hydrolysis of the compounds does not occur in the presence of AChE.

Example 37

AChE Analysis of (R)-1'-methylpyrrolidin-3'-yl 4-iodobenzoate

In Example 37, 3.2 mg of (R)-1'-methylpyrrolidin-3'-yl 4-iodobenzoate was dissolved in 2 mL of 50% acetonitrile/water. 50 μL of this solution was placed in a quartz cuvette of 1 cm path length and 1.45 mL of phosphate buffer pH 8.0 was added. The reaction was commenced with the addition of 15 μL of AChE stock solution. The absorbance was scanned over a range of 200-300 nm every 2 min for a total of 30 min. The results of this experiment generally indicate that enzymatic hydrolysis of the compounds does not occur in the presence of AChE.

Example 38

AChE Analysis of (R)-1'-methylpyrrolidin-3'-yl 4-cyanobenzoate

In Example 38, 2.2 mg of (R)-1'-methylpyrrolidin-3'-yl 4-cyanobenzoate was dissolved in 2 mL of 50% acetonitrile/water. 50 μL of this solution was placed in a quartz cuvette of 1 cm path length and 1.45 mL of phosphate buffer pH 8.0 was added. The reaction was commenced with the addition of 15 μL of AChE stock solution. The absorbance was scanned over a range of 200-300 nm every 2 min for a total of 30 min. The results of this experiment generally indicate that enzymatic hydrolysis of the compounds does not occur in the presence of AChE.

Examples 39-54

Butyrylcholinesterase In Vitro Assay

In Examples 39-54, interaction of the ligands with BuChE was determined by measuring the rate of the hydrolysis of the ligand in a buffered solution containing the enzyme. All ligands used in the assay were dissolved in a minimal amount of acetonitrile to form a ligand solution. 0.1 M Phosphate buffer PH 8.0 was prepared as to the above specifications. The Assay was carried out by mixing 0.1 μmol of ligand solution with 5 μL of BuChE stock solution and bringing the volume in a quartz cuvette of 1 cm path length to 1.5 mL with phosphate buffer. Scans using an UltraSpec 2100 Pro UV/Visible spectrophotometer over a wavelength of 200-900 nm monitored the rate of hydrolysis of the ligand by the enzyme. Change of absorbance in the spectrum indicated hydrolysis of the ligand by the enzyme. The results of these experiments generally indicate that enzymatic hydrolysis of the compounds does occur in the presence of BuChE. Coupled with the results of the experiments of Examples 23-38, these results indicates that the compounds disclosed herein generally bind selectively to the enzymatic site of BuChE and not to that of AChE.

Example 39

BuChE analysis of (1,2 dihydro-2-oxopyridin-3-yl)methyl 4-iodobenzoate

In Example 39, 3.5 mg of (1,2 dihydro-2-oxopyridin-3-yl) methyl 4-iodobenzoate was dissolved in 20 mL of acetonitrile. 100 μL of this solution was placed in a quartz cuvette of 1 cm path length and 1.40 mL of phosphate buffer pH 8.0 was added. The reaction was commenced with the addition of 5 μL of BuChE stock solution. The absorbance was scanned over a range of 200-900 nm every 2 min sec for a total of 30 min. The results of this experiment generally indicate that enzymatic hydrolysis of the compounds does occur in the presence of BuChE.

Example 40

BuChE analysis of (1,2-dihydro-2-oxopyridin-3-yl)methyl 4-fluorobenzoate

In Example 40, 6.5 mg of (1,2 dihydro-2-oxopyridin-3-yl) methyl 4-fluorobenzoate was dissolved in 10 mL of acetonitrile. 100 μL of this solution was placed in a quartz cuvette of 1 cm path length and 1.40 mL of phosphate buffer pH 8.0 was added. The reaction was commenced with the addition of 5 μL of BuChE stock solution. The absorbance was scanned over a range of 200-900 nm every 1 min for a total of 20 min. The results of this experiment generally indicate that enzymatic hydrolysis of the compounds does occur in the presence of BuChE.

Example 41

BuChE analysis of (1,2-dihydro-2-oxopyridin-3-yl)methyl 4-cyanobenzoate

In Example 41, 2.5 mg of (1,2 dihydro-2-oxopyridin-3-yl) methyl 4-cyanobenzoate was dissolved in 15 mL of acetonitrile. 100 μL of this solution was placed in a quartz cuvette of 1 cm path length and 1.40 mL of phosphate buffer pH 8.0 was added. The reaction was commenced with the addition of 5 μL of BuChE stock solution. The absorbance was scanned over a range of 200-900 nm every 2 min for a total of 30 min. The results of this experiment generally indicate that enzymatic hydrolysis of the compounds does occur in the presence of BuChE.

Example 42

BuChE analysis of
(1,6-dihydro-6-oxopyridin-2-yl)methyl
4-iodobenzoate

In Example 42, 3.5 mg of (1,6 dihydro-6-oxopyridin-2-yl) methyl 4-iodobenzoate was dissolved in 20 mL of acetonitrile. 100 µL of this solution was placed in a quartz cuvette of 1 cm path length and 1.40 mL of phosphate buffer pH 8.0 was added. The reaction was commenced with the addition of 5 µL of BuChE stock solution. The absorbance was scanned over a range of 200-900 nm every 20 sec for a total of 5 min. The results of this experiment generally indicate that enzymatic hydrolysis of the compounds does occur in the presence of BuChE.

Example 43

BuChE analysis of
(1,6-dihydro-6-oxopyridin-2-yl)methyl
4-fluorobenzoate

In Example 43, 2.7 mg of (1,6-dihydro-6-oxopyridin-2-yl) methyl 4-fluorobenzoate was dissolved in 10 mL of acetonitrile. 100 µL of this solution was placed in a quartz cuvette of 1 cm path length and 1.40 mL of phosphate buffer pH 8.0 was added. The reaction was commenced with the addition of 5 µL of BuChE stock solution. The absorbance was scanned over a range of 200-900 nm every 30 sec for a total of 7.5 min. The results of this experiment generally indicate that enzymatic hydrolysis of the compounds does occur in the presence of BuChE.

Example 44

BuChE analysis of
(1,6-dihydro-6-oxopyridin-2-yl)methyl
4-cyanobenzoate

In Example 44, 2.5 mg of (1,6 dihydro-6-oxopyridin-2-yl) methyl 4-cyanobenzoate was dissolved in 8 mL of acetonitrile. 100 µL of this solution was placed in a quartz cuvette of 1 cm path length and 1.40 mL of phosphate buffer pH 8.0 was added. The reaction was commenced with the addition of 54 of BuChE stock solution. The absorbance was scanned over a range of 200-900 nm every 30 sec for a total of 7.5 min. The results of this experiment generally indicate that enzymatic hydrolysis of the compounds does occur in the presence of BuChE.

Example 45

BuChE analysis of 1'-methylpiperidin-4'-yl
4-iodobenzoate

In Example 45, 1.8 mg of 1'-methylpiperidin-4'-yl-4-iodobenzoate was dissolved in 2 mL of 50% acetonitrile/water. 50 µL of this solution was placed in a quartz cuvette of 1 cm path length and 1.45 mL of phosphate buffer pH 8.0 was added. The reaction was commenced with the addition of 15 µL of 30% BuChE stock solution. The absorbance was scanned over a range of 200-300 nm every 2 min for a total of 30 min. The results of this experiment generally indicate that enzymatic hydrolysis of the compounds does occur in the presence of BuChE.

Example 46

BuChE analysis of 1'-methylpiperidin-4'-yl
4-fluorobenzoate

In Example 46, 2.4 mg of 1'-methylpiperidin-4'-yl-4-fluorobenzoate was dissolved in 2 mL of 50% acetonitrile/water. 50 µL of this solution was placed in a quartz cuvette of 1 cm path length and 1.45 mL of phosphate buffer pH 8.0 was added. The reaction was commenced with the addition of 154 of 30% BuChE stock solution. The absorbance was scanned over a range of 200-300 nm every 2 min for a total of 30 min. The results of this experiment generally indicate that enzymatic hydrolysis of the compounds does occur in the presence of BuChE.

Example 47

BuChE analysis of 1'-methylpiperidin-4'-yl
4-cyanobenzoate

In Example 47, 2.4 mg of 1'-methylpiperidin-4'-yl-4-cyanobenzoate was dissolved in 2 mL of 50% acetonitrile/water. 50 µL of this solution was placed in a quartz cuvette of 1 cm path length and 1.45 mL of phosphate buffer pH 8.0 was added. The reaction was commenced with the addition of 15 µL of 30% BuChE stock solution. The absorbance was scanned over a range of 200-300 nm every 2 min for a total of 30 min. The results of this experiment generally indicate that enzymatic hydrolysis of the compounds does occur in the presence of BuChE.

Example 48

BuChE analysis of 1'-methylpiperidin-4'-yl benzoate

In Example 48, 2.2 mg of 1'-methylpiperidin-4'-yl benzoate was dissolved in 2 mL of 50% acetonitrile/water. 50 µL of this solution was placed in a quartz cuvette of 1 cm path length and 1.45 mL of phosphate buffer pH 8.0 was added. The reaction was commenced with the addition of 15 µL of 30% BuChE stock solution. The absorbance was scanned over a range of 200-300 nm every 2 min for a total of 30 min. The results of this experiment generally indicate that enzymatic hydrolysis of the compounds does occur in the presence of BuChE.

Example 49

BuChE analysis of 1'-methylpiperidin-4'-yl
3-iodobenzoate

In Example 49, 1'-methylpiperidin-4'-yl 3-iodobenzoate was tested according to the procedure set forth above in Example 39. The results of this experiment generally indicate that enzymatic hydrolysis of the compounds does occur in the presence of BuChE.

Example 50

BuChE analysis of 1'-methylpiperidin-4'-yl
3-cyanobenzoate

In Example 50, 1'-methylpiperidin-4'-yl 3-cyanobenzoate was tested according to the procedure set forth in Example 39. The results of this experiment generally indicate that enzymatic hydrolysis of the compounds does occur in the presence of BuChE.

Example 51

BuChE analysis of (S)-1'-methylpyrrolidin-3'-yl 4-iodobenzoate

In Example 51, 3.2 mg of 1'-methylpiperidin-3'-yl 4-iodobenzoate was dissolved in 2 mL of 50% acetonitrile/water. 50 µL of this solution was placed in a quartz cuvette of 1 cm path length and 1.45 mL of phosphate buffer pH 8.0 was added. The reaction was commenced with the addition of 15 µL of 30% BuChE stock solution. The absorbance was scanned over a range of 200-300 nm every 2 min for a total of 30 min. The results of this experiment generally indicate that enzymatic hydrolysis of the compounds does occur in the presence of BuChE.

Example 52

BuChE analysis of (S)-1'-methylpyrrolidin-3'-yl 4-cyanobenzoate

In Example 52, 2.3 mg of (S)-1'-methylpyrrolidin-3'-yl 4-cyanobenzoate was dissolved in 2 mL of 50% acetonitrile/water. 50 µL of this solution was placed in a quartz cuvette of 1 cm path length and 1.45 mL of phosphate buffer pH 8.0 was added. The reaction was commenced with the addition of 15 µL of 30% BuChE stock solution. The absorbance was scanned over a range of 200-300 nm every 2 min for a total of 30 min. The results of this experiment generally indicate that enzymatic hydrolysis of the compounds does occur in the presence of BuChE.

Example 53

BuChE analysis of (R)-1'-methylpyrrolidin-3'-yl-4-iodobenzoate

In Example 53, 3.2 mg of (R)-1'-methylpyrrolidin-3'-yl 4-iodobenzoate was dissolved in 2 mL of 50% acetonitrile/water. 50 µL of this solution was placed in a quartz cuvette of 1 cm path length and 1.45 mL of phosphate buffer pH 8.0 was added. The reaction was commenced with the addition of 15 µL of 30% BuChE stock solution. The absorbance was scanned over a range of 200-300 nm every 2 min for a total of 30 min. The results of this experiment generally indicate that enzymatic hydrolysis of the compounds does occur in the presence of BuChE.

Example 54

BuChE analysis of (R)-1'-methylpyrrolidin-3'-yl 4-cyanobenzoate

In Example 54, 2.2 mg of (R)-1'-methylpyrrolidin-3'-yl 4-cyanobenzoate was dissolved in 2 mL of 50% acetonitrile/water. 50 µL of this solution was placed in a quartz cuvette of 1 cm path length and 1.45 mL of phosphate buffer pH 8.0 was added. The reaction was commenced with the addition of 15 µL of 30% BuChE stock solution. The absorbance was scanned over a range of 200-300 nm every 2 min for a total of 30 min. The results of this experiment generally indicate that enzymatic hydrolysis of the compounds does occur in the presence of BuChE. The results of this experiment generally indicate that enzymatic hydrolysis of the compounds does occur in the presence of BuChE.

Example 55

Michaelis-Menten Constant and Maximum Reaction Velocity Measurement

In Example 55, $K_m$ and relative $V_{max}$ values were determined for compounds identified to be hydrolyzed by BuChE. The assay was carried out by mixing 1 uL of BuChE stock solution in 1.4 mL of phosphate buffer. Absorbance of this solution was calibrated to zero and the reaction commenced with the addition of 100 µL of a solution of ligand in 100% acetonitrile. The reactions were carried out at room temperature. The rate of change of absorbance (ΔA/min), reflecting the rate of hydrolysis of the ligand by enzyme was recorded every 3 seconds for a total of 36 seconds using a Milton-Roy uv-visible spectrophotometer set at λ=285 nm.

A Lineweaver-Burk plot was used in order to determine the $K_m$ (substrate concentration at which the reaction rate reaches half of its maximum value), and relative $V_{max}$ (maximum reaction velocity), values. Average Michealis-Menten constant and maximum reaction velocity values for a selection compounds (N=3) were measured, and the results are set forth in Table 1 below. $K_m$ value for butyrylthiocholine in the presence of BuChE is 30.6±7.0 µM:

TABLE 1

$K_m$ and $V_{max}$ Values

| | Compound | $K_m$ (µM) | $V_{max}$ (ΔA min$^{-1}$) |
|---|---|---|---|
| 1 | 1-methylpiperidin-4-yl 4-iodobenzoate (Ex. 7) | 26 ± 2 | 8.4 ± 0.4 |
| 2 | 1-methylpiperidin-4-yl 4-fluorobenzoate (Ex. 8) | 753 ± 115 | 36 ± 6 |
| 3 | 1-methylpiperidin-4-yl 4-cyanobenzoate (Ex. 9) | 48 ± 18 | 12 ± 3 |
| 4 | 1-methylpiperidin-4-yl benzoate (Ex. 10) | 68 ± 9 | 6.8 ± 0.5 |
| 5 | I-(-)-1-methylpyrrolidin-3-yl 4-iodobenzoate (Ex 16) | 144 ± 121 | 10 ± 9 |
| 6 | I-(-)-1-methylpyrrolidin-3-yl 4-cyanobenzoate (Ex 17) | 198 ± 18 | 30 ± 3 |
| 7 | (S)-(+)-1-methylpyrrolidin-3-yl 4-iodobenzoate (Ex 14) | 16 ± 4 | 6.1 ± 0.5 |
| 8 | (S)-(+)-1-methylpyrrolidin-3-yl 4-cyanobenzoate (Ex 15) | 200 ± 52 | 16 ± 4 |
| 9 | (6-oxo-1,6-dihydropyridin-2-yl)methyl 4-iodobenzoate | 40.8 ± 8.5 | 9.7 ± 1.7 |

Example 56

SPECT Imaging Using (6-oxo-1,6-dihydropyridin-2-yl)methyl-4-$^{123}$iodobenzoate Shortly after the synthesis and purification detailed in Example 21, a rat was injected with the radiolabeled compound (6-oxo-1,6-dihydropyridin-2-yl)methyl-4-$^{123}$iodobenzoate and SPECT images were taken at regular time points for several hours.

Figure 4:
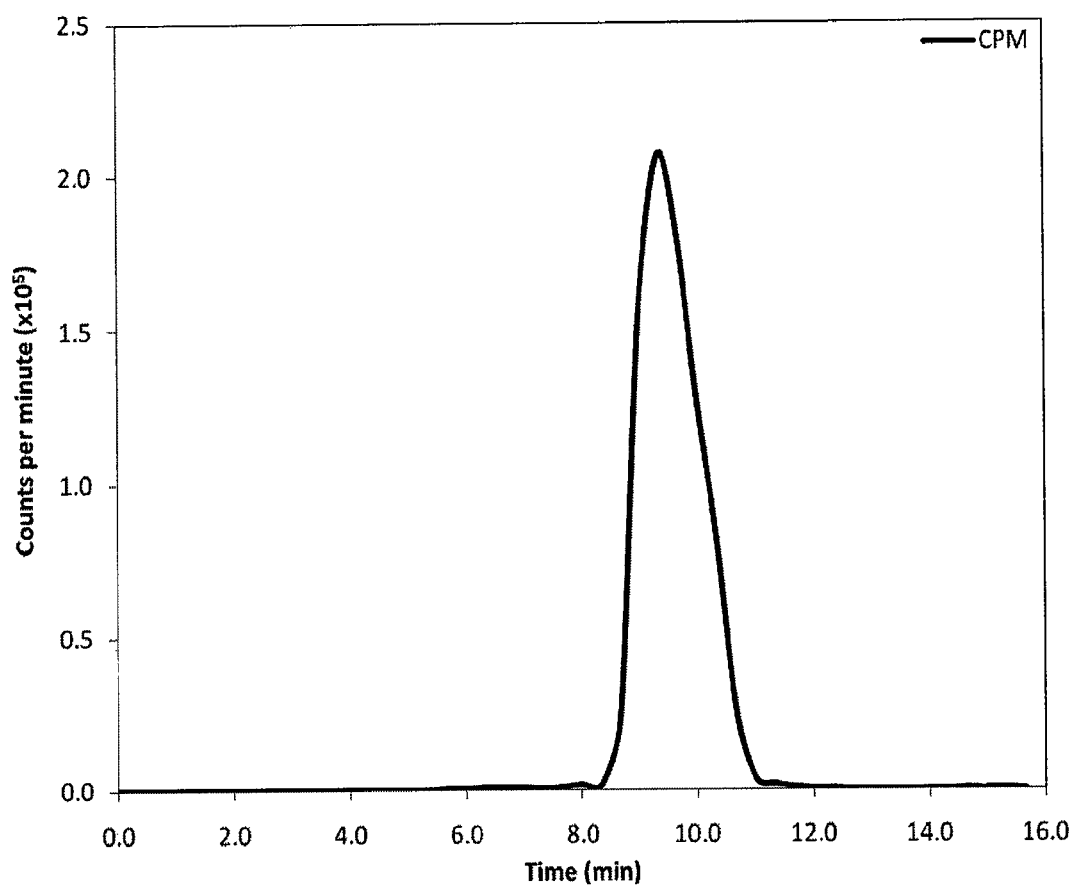
FIG. 4 is the scintillation count from HPLC purification and collection of (1,6-dihydro-6-oxopyridin-2-yl)methyl 4-[123]iodobenzoate. Radioactivity elution time was consistent with UV/Vis absorbance corresponding to the product.

After imaging, the rat was sacrificed and perfused. Radiation counts from HPLC attributable to (1,6-dihydro-6-oxopyridin-2-yl)methyl 4-$^{123}$iodobenzoate remaining in the brain fraction are shown in FIG. 4. This result indicates that the compound penetrates into the brain and can be imaged.

EQUIVALENTS

Upon examination of this disclosure, individuals skilled in the art may recognize certain equivalents to those described herein, which are meant to be encompassed by the following claims.

The disclosures of all published references and patents cited herein are hereby incorporated by reference in their entireties.

We claim:

1. A compound of Formula I and pharmaceutically acceptable salts, stereo-isomers, polymorphs, metabolites, pro-drugs and combinations thereof:

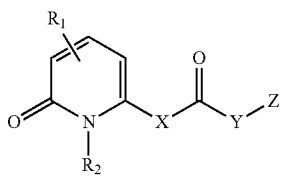

(I)

wherein $R_1$ is selected from the group consisting of hydrogen, fluoro, iodo, alkyl, and aryl; $R_2$ is selected from the group consisting of hydrogen, alkyl, and aryl;

X is selected from the group consisting of $CH_2$, $CH_2O$, oxygen, $OCH_2$, $CH_2S$, $SCH_2$, NH, N-alkyl, and N-aryl;

Y is an optional spacer group, absent or selected from the group consisting of oxygen, sulfur, NH, N-alkyl, and N-aryl; and Z is selected from the group consisting of alkyl substituted with cyano, fluoro, or iodo and aryl substituted with cyano, fluoro, or iodo; with the exception that if Y is absent or NH, then X cannot be NH.

2. The compound of claim 1, wherein $R_1$ and $R_2$ are both hydrogen, X is $CH_2O$, Y is absent, and Z is selected from the group consisting of fluorophenyl, cyanophenyl, and iodophenyl.

3. The compound of claim 2, wherein Z is selected from the group consisting of $^{18}$F-phenyl, $^{123}$I-phenyl, and $^{131}$I-phenyl.

4. The compound of claim 1, which is (6-oxo-1,6-dihydropyridin-2-yl)methyl 4-[123]iodobenzoate.

5. A method of early detection of a neurological condition, comprising:
   administering to a subject an effective quantity of a butyrylcholinesterase-specific compound of Formula I according to claim 1 and pharmaceutically acceptable salts, stereo-isomers, polymorphs, metabolites, pro-drugs and combinations thereof:

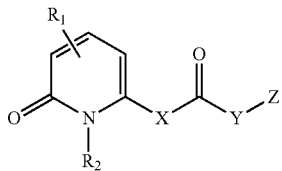

(I)

wherein $R_1$ is selected from the group consisting of hydrogen, fluoro, iodo, alkyl, and aryl; $R_2$ is selected from the group consisting of hydrogen, alkyl, and aryl;

X is selected from the group consisting of $CH_2$, $CH_2O$, oxygen, $OCH_2$, $CH_2S$, $SCH_2$, NH, N-alkyl, and N-aryl;

Y is an optional spacer group, absent or selected from the group consisting of oxygen, sulfur, NH, N-alkyl, and N-aryl; and Z is selected from the group consisting of alkyl substituted with cyano, fluoro, or iodo and aryl substituted with cyano, fluoro, or iodo; with the exception that if Y is absent or NH, then X cannot be NH;

imaging the brain of said subject to identify the position and relative abundance of said compound in vivo utilizing a scan selected from the group consisting of CT, PET, and SPECT;

and distinguishing said position and relative abundance from reference cases to determine subject's diagnosis.

6. The method of claim 5, in which the butyrylcholinesterase-specific compound is (6-oxo-1,6-dihydropyridin-2-yl) methyl 4-[123]iodobenzoate.

7. The method of claim 5, in which the neurological condition is Alzheimer's disease and related dementias.

8. The method of claim 5, in which the neurological condition is multiple sclerosis.

9. The method of claim 5, in which the neurological condition is malignant brain tumor.

10. The method of claim 5, in which the subject is a human.

11. The method of claim 5, wherein the butyrylcholinesterase-specific compound is radiolabeled on a functional group of the compound that remains in contact with the BuChE after enzymatic cleavage of the compound.

12. The compound of claim 5, wherein $R_1$ and $R_2$ are both hydrogen, X is $CH_2O$, Y is absent, and Z is selected from the group consisting of fluorophenyl, cyanophenyl, and iodophenyl.

13. The compound of claim 12, wherein Z is selected from the group consisting of $^{18}$F-phenyl, $^{123}$I-phenyl, and $^{131}$I-phenyl.

14. A method of treatment of a neurological condition, comprising:
   administering to a subject in need thereof, an effective quantity of a butyrylcholinesterase-specific compound of Formula I according to claim 1 and pharmaceutically acceptable salts, stereo-isomers, polymorphs, metabolites, pro-drugs and combinations thereof:

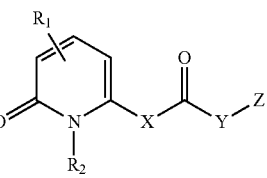

(I)

wherein $R_1$ is selected from the group consisting of hydrogen, fluoro, iodo, alkyl, and aryl; $R_2$ is selected from the group consisting of hydrogen, alkyl, and aryl;

X is selected from the group consisting of $CH_2$, $CH_2O$, oxygen, $OCH_2$, $CH_2S$, $SCH_2$, NH, N-alkyl, and N-aryl;

Y is an optional spacer group, absent or selected from the group consisting of oxygen, sulfur, NH, N-alkyl, and N-aryl; and Z is selected from the group consisting of alkyl substituted with cyano, fluoro, or iodo and aryl substituted with cyano, fluoro, or iodo; with the exception that if Y is absent or NH, then X cannot be NH.

15. The method of claim 14, in which the butyrylcholinesterase-specific compound is (6-oxo-1,6-dihydropyridin-2-yl) methyl 4-iodobenzoate.

16. The method of claim 14, in which the neurological condition is Alzheimer's disease and related dementias.

17. The method of claim 14, in which the neurological condition is multiple sclerosis.

18. The method of claim 14, in which the neurological condition is malignant brain tumor.

19. The method of claim 14, in which the subject is a human.

20. The compound of claim 14, wherein $R_1$ and $R_2$ are both hydrogen, X is $CH_2O$, Y is absent, and Z is selected from the group consisting of fluorophenyl, cyanophenyl, and iodophenyl.

21. The compound of claim 20, wherein Z is selected from the group consisting of $^{18}$F-phenyl, $^{123}$I-phenyl, and $^{131}$I-phenyl.

* * * * *

UNITED STATES PATENT AND TRADEMARK OFFICE
CERTIFICATE OF CORRECTION

PATENT NO. : 8,795,630 B2
APPLICATION NO. : 13/061000
DATED : August 5, 2014
INVENTOR(S) : Sultan Darvesh et al.

It is certified that error appears in the above-identified patent and that said Letters Patent is hereby corrected as shown below:

On the Title Page

Column 1, Item (60) Related U.S. Application Data should be;
(60) Provisional application No. 61/092,861, filed on Aug. 29, 2008

Signed and Sealed this
Second Day of April, 2024

Katherine Kelly Vidal
*Director of the United States Patent and Trademark Office*